United States Patent
Kantarci et al.

(10) Patent No.: US 11,903,998 B2
(45) Date of Patent: Feb. 20, 2024

(54) COMPOSITIONS AND METHODS OF TREATING CANCER USING LIPID AGONISTS AND RECEPTORS THEREOF

(71) Applicant: Forsyth Dental Infirmary for Children, Cambridge, MA (US)

(72) Inventors: Alpdogan Kantarci, Brighton, MA (US); Shevali Kansal, Quincy, MA (US); Hatice Hasturk, Brighton, MA (US); Thomas E. Van Dyke, West Roxbury, MA (US)

(73) Assignee: Forsyth Dental Infirmary for Children, Cambridge, MA (US)

( * ) Notice: Subject to any disclaimer, the term of this patent is extended or adjusted under 35 U.S.C. 154(b) by 450 days.

(21) Appl. No.: 16/304,983

(22) PCT Filed: May 25, 2017

(86) PCT No.: PCT/US2017/034401
§ 371 (c)(1),
(2) Date: Nov. 27, 2018

(87) PCT Pub. No.: WO2017/205582
PCT Pub. Date: Nov. 30, 2017

(65) Prior Publication Data
US 2020/0330551 A1     Oct. 22, 2020

Related U.S. Application Data

(60) Provisional application No. 62/342,631, filed on May 27, 2016.

(51) Int. Cl.
| | |
|---|---|
| *A61K 38/17* | (2006.01) |
| *A61P 35/00* | (2006.01) |
| *A61K 33/243* | (2019.01) |
| *A61K 9/00* | (2006.01) |
| *A61K 31/202* | (2006.01) |
| *A61K 45/06* | (2006.01) |

(52) U.S. Cl.
CPC .......... *A61K 38/177* (2013.01); *A61K 9/0019* (2013.01); *A61K 31/202* (2013.01); *A61K 33/243* (2019.01); *A61K 45/06* (2013.01); *A61P 35/00* (2018.01)

(58) Field of Classification Search
CPC .... A61K 45/06; A61K 9/0019; A61K 31/202; A61K 38/177; A61K 33/243; A61P 35/00
See application file for complete search history.

(56) References Cited

U.S. PATENT DOCUMENTS

2020/0330551 A1   10/2020 Kantarci et al.

FOREIGN PATENT DOCUMENTS

| WO | WO-2008/058274 A2 | 5/2008 |
| WO | WO-2008/132153 A1 | 11/2008 |

OTHER PUBLICATIONS

Lee et al., Resolvin D1 inhibits TGF-1-induced epithelial mesenchymaltransition of A549 lung cancer cells via lipoxin A4 receptor/formylpeptide receptor 2 and GPR32. The International Journal of Biochemistry & Cell Biology 45: 2801-2807, 2013.*
Bai et al., Inhibition of lung cancer growth and metastasis by DHA and its metabolite, RvD1, through miR-138-5p/FOXC1 pathway. J Exp Clin Cancer Res 38(1):479, 2019.*
Ye et al., Anti-cancer and analgesic effects of resolvin D2 in oral squamous cell carcinoma. Neuropharmacology 139:182-193, 2018.*
Extended European Search Report for EP Application No. 17803557.2 dated Feb. 25, 2020.
Gao et al., "Resolvin E1 and Chemokine-like Receptor 1 Mediate Bone Preservation," The Journal of Immunology, 190(2): 689-694 (2013).
Gasterdelo et al., "Inflammation and Cancer: Role of Annexin A1 and FPR2/ALX in Proliferation and Metstatis in Human Laryngeal Squamos Cell Carcinoma," Plos One, 9(12): e111317 (2014).
International Preliminary Report on Patentability for International Application No. PCT/US2017/034401 dated Nov. 27, 2018.
International Search Report and Written Opinion for International Application No. PCT/US2017/034401 dated Sep. 14, 2017.
Janakiram et al., "Role of lipoxins, resolvins, and other bioactive lipids in colon and pancreatic cancer," Cancer Metastasis, 30(3-4): 507-523 (2011).
Ji et al., "Emerging roles of resolvins in the resolution of inflamation and pain," Trends in Neurosciences, 34(11): 599-609 (2011).
Lappano et al., "GPCRs and cancer," Acta Pharmacol Sinica, 33(3):351-362 (2012).
Serhan et al., "Resolving inflammation: dual anti-inflammatory and pro-resolution lipid mediators," Nature Reviews, 8(5): 349-361 (2008).
Tucker et al., "Emerging targets in lipid-based therapy," Biochem Pharmacol, 85(5):673-688 (2013).
Uddin et al., "Resolvins: Natural agonists for resolution of pulmonary inflammation, " Progress in Lipid Research, 50(1): 75-88 (2011).

\* cited by examiner

*Primary Examiner* — Ruixiang Li
(74) *Attorney, Agent, or Firm* — Foley Hoag LLP; Hathaway P. Russell

(57) ABSTRACT

Provided herein are methods for preventing or treating cancer in a subject comprising overexpressing at least one Receptor for a lipid agonist, such as G-protein receptors for Resolvin. Such methods may be combined with administering Resolvins, or lipoxins and their analogs, of said Receptors to enhance the pro-resolution effects of the Resolvins, or lipoxins and their analogs, in the local, inflammatory environment where cancer cells are already present.

14 Claims, 11 Drawing Sheets

A

B

| Groups | Survival | No. of nodules/animal |
|---|---|---|
| WT-Vehicle | 25% | 8-10 |
| TG-Vehicle | 25% | 8-10 |
| WT-RvE1 treated | 40% | 4-6 |
| TG-RvE1 treated | 80% | 3-5 |

COMPOSITIONS AND METHODS OF TREATING CANCER USING LIPID AGONISTS AND RECEPTORS THEREOF

CROSS-REFERENCE

This application is a national stage filing under 35 U.S.C. § 371 of PCT/US17/34401, filed on May 25, 2017, which claims the benefit of U.S. Provisional Application 62/342,631, filed on May 27, 2016, The entirety of these applications are hereby incorporated by reference.

BACKGROUND OF THE INVENTION

Chronic inflammation plays an important role in carcinogenesis and development of tumors (Colotta et al., 2009, Lee et al., 2015), such as lung cancer. In addition to smoking, occupational or environmental exposure to secondhand smoke, asbestos, certain metals (chromium, cadmium, arsenic), radiation and air pollution are major risk factors for lung cancer (Ferreccio et al., 2013). Continuous exposure to these factors damages immune cells reducing resistance, and leads to inflammation (Houghton et al., 2008). In vivo and in vitro studies have documented that chronic inflammation causes cell transformation and promotes progression of lung cancer (Gomes et al., 2014). Recent studies suggest that a micro-inflammatory environment and immune cells are actively involved in oncogenesis of lung cancer (Heinrich et al., 2012, Cho et al., 2011, Conway et al., 2016).

Inflammation is characterized by recruitment of innate immune cells and release of pro-inflammatory cytokines. Cytokines function in a coordinated manner to initiates an inflammatory cascade (Coussens and Werb, 2002). Failure to resolve the acute lesion normally leads to chronic inflammation, which in turn can cause genetic damage via production of reactive oxygen (ROS) and nitrogen (RNS) species (Maderna and Godson, 2003, Buckley et al., 2001). ROS and RNS further induce the formation and accumulation of mutagenic, toxic, and/or genome-destabilizing DNA lesions that induce cell transformation (Fitzpatrick, 2001).

Inflammation contributes to malignancy through actions on tumor tissue remodeling, angiogenesis, metastasis and suppression of the innate immune response (Lu et al., 2006). Since the same functions have been identified as therapeutic targets, inflammation itself has been suggested as an important target for therapy (Shi et al., 2015). Yet, successful identification of therapeutic targets to inflammation, and clinical translation of these targets to cancer, remains a challenge (23,24).

Accordingly, there is a great need in the art to identify potential therapeutic strategies and compositions that target inflammation in the treatment of cancer.

SUMMARY OF THE INVENTION

Provided herein are methods for preventing or treating cancer in a subject comprising overexpressing at least one Receptor for a lipid agonist, such as G-protein receptors for Resolvin, such as Resolvin E1, or LO-derived eicosanoid receptors LXA4 receptor (ALX) for lipoxins, such as LXA4. Such methods may be combined with administering lipid agonists (Resolvins or lipoxins and their analogs of said Receptors) to enhance the pro-resolution effects of the lipid agonist in the local, inflammatory environment where cancer cells are already present.

One aspect of the invention relates to a method for preventing or treating cancer in a subject, the method comprising overexpressing at least one Receptor for a lipid agonist.

In some embodiments, the Receptor is a G-protein coupled receptor (GPCR).

In some embodiments, the GPCR is selected from the group consisting of receptor for Resolvin E1 (ERV1), G protein-coupled receptor 32 (GPR32), proResolvin mediator annexin A1 (ALX/FPR2), LO-derived eicosanoid receptors LXA4 receptor (ALX), and Leukotriene B4 receptor (BLT).

In some embodiments, the GPCR is ERV1.

In some embodiments, the GPCR is ALX.

In some embodiments, the Receptor is provided exogenously.

In some embodiments, the Receptor is administered to the subject.

In some embodiments, an agent is administered to increase expression of endogenous levels of the Receptor.

In some embodiments, the method further comprising the step of administering at least one lipid agonist.

In some embodiments, the lipid agonist is administered in combination with the Receptor.

In some embodiments, the lipid agonist is administered subsequently to administering the Receptor.

In some embodiments, the lipid agonist is selected from the group consisting of di-hydroxy members of the Resolvin E series, di-hydroxy members of the Resolvin D series, tri-hydroxy members of the Resolvin E series, tri-hydroxy members of the Resolvin D series, Resolvins derived from eicosapentaenoic acid (EPA), resolvins derived fromdocosahexaenoic acid (DHA), or endogenous lipoxins derived from arachidonic acid, lipoxins, and maresins.

In some embodiments, the lipid agonist is a member of the Resolvin D Series.

In some embodiments, the Resolvin D Series is selected from the group consisting of Resolvin D1, D2, D3, D4, D5, and D6.

In some embodiments, the lipid agonist is a member of the Resolvin E Series.

In some embodiments, the Resolvin E Series is selected from the group consisting of Resolvin E1, E2, and E3.

In some embodiments, the Resolvin E Series is Resolvin E1.

In some embodiments, the lipid agonist is a member of the lipoxins.

In some embodiments, the lipoxins is selected from LXA4, LXB4, or analogs thereof.

In some embodiments, the lipoxin is LXA4.

In some embodiments, the Receptor or lipid agonist is administered systematically. In some embodiments, the systematic administration is selected from the group consisting of oral, intravenous, intradermal, intraperitoneal, subcutaneous, and intramuscular administration.

In some embodiments, the composition is administered intratumorally or peritumorally.

In some embodiments, the subject is treated with at least one additional anti-cancer agent.

In some embodiments, the anti-cancer agent is selected from the group consisting of paclitaxel, cisplatin, topotecan, gemcitabine, bleomycin, etoposide, carboplatin, docetaxel, doxorubicin, topotecan, cyclophosphamide, trabectedin, olaparib, tamoxifen, letrozole, and bevacizumab.

In some embodiments, the subject is treated with at least one additional anti-cancer therapy.

In some embodiments, the anti-cancer therapy is radiation therapy, chemotherapy, or surgery.

In some embodiments, the cancer is a solid tumor.

In some embodiments, the cancer is selected from the group consisting of oral cancer, breast cancer, ovarian cancer, prostate cancer, pancreatic cancer, lung cancer, liver cancer, throat cancer, stomach cancer, and kidney cancer.

In some embodiments, the cancer is lung cancer.

In some embodiments, the subject is a mammal.

In some embodiments, the mammal is human.

In some embodiments, an inflammatory response is inhibited or reduced in the subject.

In some embodiments, the inhibition or reduction in the inflammatory response results in a decreased expression of the NF-κB, IL-6, and IL-8 genes.

In some embodiments, an angiogenic response is inhibited or reduced in the subject. In some embodiments, the inhibition or reduction in the angiogenic response results in a decreased expression of the Ang1, Ang2, and VEGF genes.

In some embodiments, the malignancy is inhibited or reduced in the subject.

In some embodiments, the tumor necrosis is enhanced or increased in the subject.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF FIGURES

FIG. 10A depicts that tumor growth was decreased in response to treatment with cisplatin in both WT and TG groups compared to control groups by more than 10-fold (please note the magnitude difference on y-axes of two panels). RvE1 significantly and further reduced the tumor volume in both WT and TG animals compared to cisplatin alone (*$p<0.001$). This difference was more significant in TG group compared to the WT group (#$p<0.05$). 10B and 10C) Cisplatin reduced COX-2 and NF-κB expression in wild type (WT) and ERV1-overexpressing transgenic (TG) mice in parallel with reduced tumor size ($p<0.001$). RvE1 increased the suppression of Cox-2 and NF-κB expression in both WT and TG animals (*$p<0.01$); this effect was more pronounced in TG animals (#$p<0.05$; n=5 per group).

DETAILED DESCRIPTION OF THE INVENTION

Figure 1:
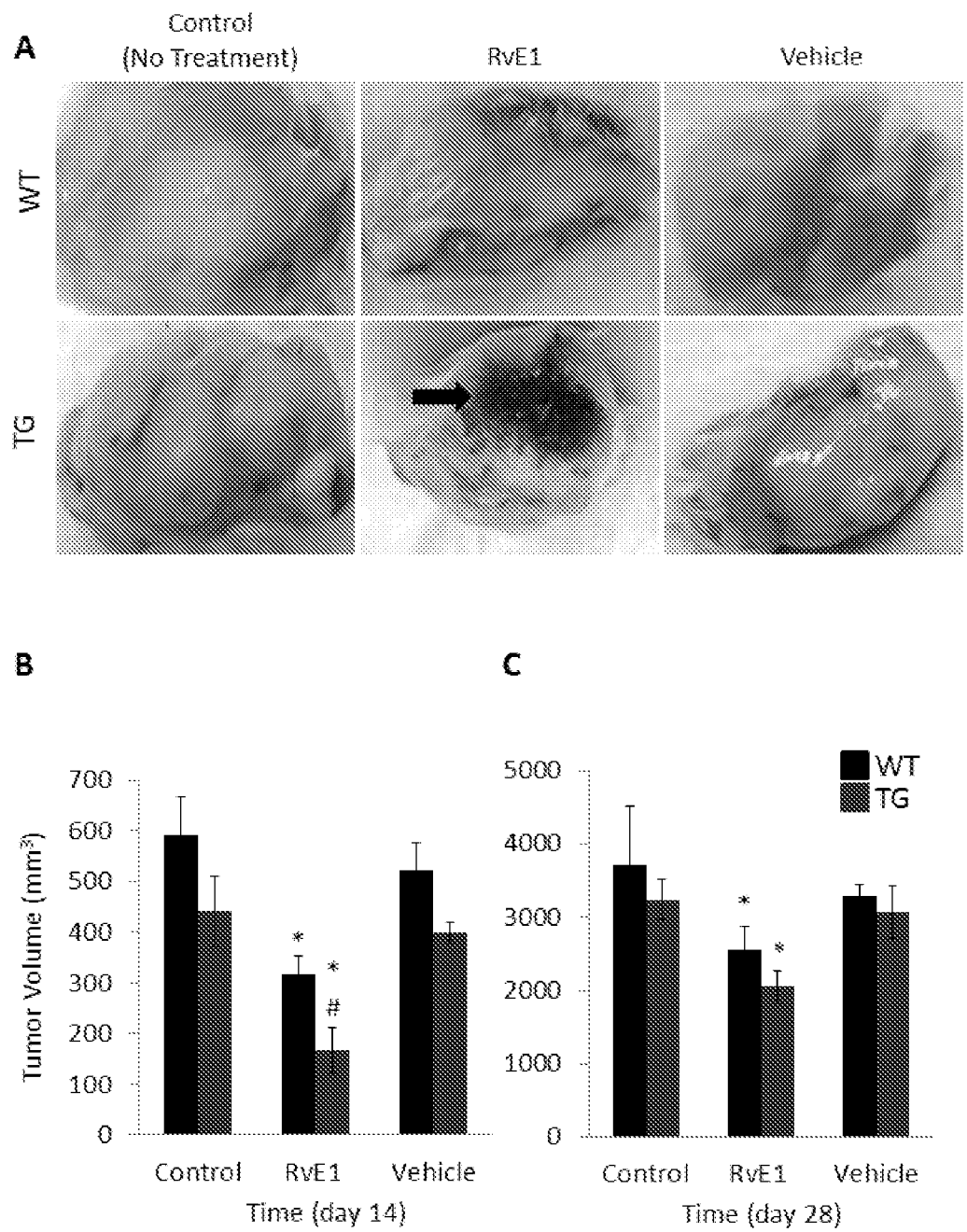
FIG. 1 depicts tumor volume in response to pre-treatment of RvE1 in Wt and Tg mice; ***$p<0.001$ as compared to Wt Control, $^{III}p<0.001$ as compared to Tg Control, $^{¥}p<0.01$ as compared to Wt RvE1.

This invention is based in part on the discovery that resolution of inflammation can prevent tumor and cancer development. In a transgenic animal model, which overexpresses the receptor for Resolvin E1 (RvE1), it was demonstrated that the overexpression of the receptor (ERV1, also formerly known as ChemR23), effectively prevents the cancer development and enhances RvE1-induced inflammatory changes at the local environment of cancer. In addition, RvE1 and its application in ERV1-transgenic (TG) animals restore the angiogenic transformation, which is a critical process during the oncogenesis and resolution of inflammation. Moreover, RvE1 improved the response to the anticancer drug (e.g., cisplatin) in a xenograft model of lung cancer. Analogously, LxA4 worked similar to RvE1. The orthotopic lung model responded well to RvE1 similar to the xenograft lung model to LXA4, and can be applicable to oral cancer models. This invention is the first time, the anti-oncogenic properties of resolution-phase agonists of inflammatory process are associated with the prevention of cancer development. This discovery will enable scientists and clinicians to develop inflammation-targeted methods for prevention and treatment of cancer development, progression, and metastasis. Other resolution-phase lipid agonists of inflammation (e.g. lipoxins, D-series Resolvins, maresins), and their respective receptors, can be effective in prevention and treatment of cancer.

A. Definitions

The articles "a" and "an" are used herein to refer to one or to more than one (i.e., to at least one) of the grammatical object of the article. By way of example, "an element" means one element or more than one element.

The term "administering" means providing a pharmaceutical agent or composition to a subject, and includes, but is not limited to, administering by a medical professional and self-administering.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, hepatocellular carcinoma (HCC), acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor.

As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. In some embodiments, the additional therapeutic compound is administered within about 5 minutes to within about 168 hours prior to or after administration of the compound of the invention. Thus, a subject who receives such treatment can benefit from a combined effect of different therapeutic compounds.

The term "inhibit" or "inhibits" means to decrease, suppress, attenuate, diminish, arrest, or stabilize the development or progression of a disease, disorder, or condition, the activity of a biological pathway, or a biological activity, such as the growth of a solid malignancy, e.g., by at least 10%, 20%, 30%, 40%, 50%, 60%, 70%, 80%, 90%, 95%, 98%, 99%, or even 100% compared to an untreated control subject, cell, biological pathway, or biological activity or compared to the target, such as a growth of a solid malignancy, in a subject before the subject is treated. By the term "decrease" is meant to inhibit, suppress, attenuate, diminish, arrest, or stabilize a symptom of a cancer disease, disorder, or condition. It will be appreciated that, although not precluded, treating a disease, disorder or condition does not require that the disease, disorder, condition or symptoms associated therewith be completely eliminated.

As used herein, "lipid agonist" refer to any resolution-phase lipid agonists of inflammation, including but not limited to any Resolvins described herein, such as di-hydroxy members of the Resolvin E series, di-hydroxy members of the Resolvin D series, tri-hydroxy members of the Resolvin E series, tri-hydroxy members of the Resolvin D series, Resolvins derived from eicosapentaenoic acid (EPA), esolvins derived fromdocosahexaenoic acid (DHA), or endogenous lipoxins derived from arachidonic acid, lipoxins, and maresins.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically-acceptable salts" refers to the relatively non-toxic, inorganic and organic acid addition salts of compounds.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

A "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

The term "subject in need thereof" means a subject identified as in need of a therapy or treatment.

The terms "systemic administration," "administered systemically," "peripheral administration," and "administered peripherally" mean the administration of a compound, drug or other material other than directly into the central nervous system, such that it enters the patient's system and, thus, is subject to metabolism and other like processes, for example, subcutaneous administration.

The term "therapeutic agent" or "pharmaceutical agent" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents is known in the art and may be identified by their effects. Certain therapeutic agents are capable of regulating red cell proliferation and differentiation. Examples include chemotherapeutic nucleotides, drugs, hormones, non-specific (e.g. non-antibody) proteins, oligonucleotides (e.g., antisense oligonucleotides that bind to a target nucleic acid sequence (e.g., mRNA sequence)), peptides, and peptidomimetics.

The term "therapeutic effect" refers to a local or systemic effect in animals, particularly mammals, and more particularly humans, caused by a pharmacologically active substance.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The term "treating" a disease in a subject or "treating" a subject having a disease refers to subjecting the subject to a pharmaceutical treatment, e.g., the administration of a Resolvin and/or Resolvin Receptor, such that at least one symptom of the disease is decreased, prevented from worsening, or delayed from worsening.

The terms "tumor," "solid malignancy," or "neoplasm" refer to a lesion that is formed by an abnormal or unregulated growth of cells. Preferably, the tumor is malignant, such as that formed by a cancer.

B. Resolvins

The methods of the present invention include administration of at least one lipid agonist, such as Resolvin. As used herein the term "Resolvin" encompasses Resolvins, Resolvin derivatives and analogs, as well as physiologically acceptable salts and prodrugs thereof. In certain embodiments, a single Resolvin is administered to the subject. In other embodiments, two or more Resolvins are administered to the subject. In such embodiments, administration of the Resolvins may be simultaneous (i.e., administration at essentially the same time, e.g., in the form of a mixture of Resolvins) or sequential (i.e., administration of the different Resolvins at different times).

Resolvins are compounds generated from the interactions between a dietary omega-3-polyunsaturated fatty acid (PUFA) such as eicosapentaenoic acid (EPA) or docosahexaenoic acid (DHA), cyclooxygenase-II (COX-2) and an analgesic, such as aspirin ASA. It was recently demonstrated that ASA treatment of murine in vivo and human tissues in vitro carrying COX-2 initiates the production of novel 17R-hydroxy series docosanoids via previously undescribed pro-inflammatory responses (i.e., cytokine production, peritonitis). During stress, these cellular pathways utilize omega-3 fatty acids to biosynthesize endogenous compounds that serve in anti-inflammation signaling. These new di- and tri-hydroxy-containing compounds derived from omega-3 fatty acids were termed "Resolvins", because they (a) are formed within the resolution phase of acute inflammatory response, at least in part, as cell-cell interactions products, (b) "stop" neutrophil entry to sites of inflammation, and (c) reduce exudates (C. N. Serhan et al., J. Exp. Med., 2002, 196: 1025-1037).

Compounds derived from eicosapentaenoic acid are designated as belonging to the E series, given their EPA precursor, and denoted as Resolvins of the E series (e.g., Resolvin E1 or RvE1). Compounds derived from docosahexaenoic acid are denoted as Resolvins of the D series (e.g., Resolvin D1 or RvD1).

Resolvins suitable for use in the methods of the present invention can be any member of the family of compounds known as Resolvins, for example, as described in U.S. Pat. No. 6,949,664; U.S. Pat. Appln. Nos. 2005-0238589, 2005-0228047, 2005-0075398, 2004-0116408; and 2003-0191184; PCT application Nos. WO 2005/089744, WO 2005/013908, WO 2004/014835, WO 2003/084305, and WO 2003/053423; and European Pat. Appln. No. EP 1 537 067 (each of which is incorporated herein by reference in its entirety). Other suitable Resolvins include those described, for example, in C. N. Serhan et al., J. Exp. Med., 2002, 196: 1025-1037; S. Hong et al., J. Biol. Chem., 2003, 278: 14677-14687; V. L. Marcheselli et al., J. Biol. Chem., 2003, 278: 43807-43817; C. N. Serhan and N. Chiang, Rheum. Dis. Clin. North Am., 2004, 30: 69-95; C. N. Serhan et al., Prostaglandins Other Lipid Mediat., 2004, 73: 155-172; C. N. Serhan et al., Histochem. Cell Biol., 2004, 122: 305-321; C. N. Serhan et al., Lipid, 2004, 39: 1125-1132; C. N. Serhan, Pharmacol. Ther., 2005, 105: 7-21; C. N. Serhan, Curr. Opin. Clin. Nutr. Metab. Care, 2005, 8: 115-121; G. L. Bannenberg et al., J. Immunol., 2005, 174: 4345-4355; U. N. Das, Med. Sci. Monit., 2005, 11: RA233-237; and U. N. Das, J. Assoc. Physicians India, 2005, 53: 623-527; each of which is incorporated herein by reference in its entirety).

In certain embodiments, Resolvin E1 is used for preventing inflammation and vascularization resulting in tumor necrosis. Resolvin E1 belongs to an array of natural bioactive lipids that are generated in vivo from omega-3 polyunsaturated fatty acids by aspirin modified COX-2 (C. N. Serhan et al., J. Exp. Med., 2000, 192: 1197; C. N. Serhan et al., J. Exp. Med., 2002, 196: 1025). The Examples section below describes experiments in which Resolvin E1 is used. RvE1 facilitates its biological functions such as the clearance of neutrophils by binding to the receptors BLT-1 on neutrophils and ERV1 (formerly chemR23) on other myeloid cells (Arita et al., 2006)

Resolvins used in the methods and compositions of the present invention may be prepared in vivo or in vitro and then substantially purified and isolated by techniques known in the art (see, for example, U.S. Pat. No. 6,670,396, which is incorporated herein by reference in its entirety). Without limitation, the purity of the compounds is generally at least about 90%, preferably at least about 95%, and most preferably at least about 99%. Certain Resolvins used in the inventive methods may be prepared by chemically modifying one or more purified compounds. For example, a purified compound may be chemically modified into a pharmaceutically acceptable salt or prodrug. Additionally or alternatively, one or more hydroxy, thiol or amino groups of the molecule may be protected using methods well known in the art. Resolvins can also be manufactured independently using conventional synthetic methods. For example, Resolvins may be selected from the group consisting of di-hydroxy members of the Resolvin E series, di-hydroxy members of the Resolvin D series, tri-hydroxy members of the Resolvin E series, tri-hydroxy members of the Resolvin D series, and combinations thereof. For example, Resolvin E series include but not limited to Resolvin E1, E2, and E3. In some embodiments, Resolvin D series include but not limited to Resolvin D1, D2, D3, D4, D5, and D6. Other Resolvins may include those derived from eicosapentaenoic acid (EPA), docosahexaenoic acid (DHA), or endogenous lipoxins derived from arachidonic acid. Other resolution-phase lipid agonists of inflammation, such as lipoxins, D-series Resolvins, and maresins, are contemplated.

C. LXA4, LXA4 Analogs, and Oral Formulations Thereof

Lipoxins are naturally-occurring lipid mediators derived from the fatty acid, arachidonic acid (Bazan (2006) in *Basic Neurochemistry: Molecular, Cellular and Medical Aspects, 7th edition,* G. Siegel et al. (eds.), Chapter 33:575-591; Mattson and Bazan (2006) in *Basic Neurochemistry: Molecular, Cellular and Medical Aspects, 7th edition,* G. Siegel et al. (eds.), Chapter 35:603-615. Lipoxins are potent mediators of the resolution phase of the inflammatory response and of dysfunctional immunity (Serhan et al. (1999) *Adv. Exp. Med. Biol.* 469:287-293; Fiorucci et al. (2004) *Proc. Natl. Acad. Sci. USA.* 101:15736-15741). There are several classes of lipoxins, such as $LXA_4$ and $LXB_4$, as well as analogs thereof that have been discovered/synthesized since the initial discovery of lipoxins in the 1980s. Specifically, lipoxin $A_4$ and its analogs, including lipoxin $A_4$ epimer 15 (or 15-epi-lipoxin A4), are well known in the art (U.S. Pat. Nos. 6,831,186; 6,645,978; and 8,093,417; U.S. Pat. Publ. 2012/0149771; Fierro et al. (2003) *J Immunol.* 170:2688-2694; Bannenberg et al. (2004) *Brit. J. Pharma.* 143:43-52; and Scalia et al. (1997) *Proc. Natl. Acad. Sci. USA* 94:9967-9972).

LXA4 analogs are also well known in the art. Benzo-lipoxins have been found to be thermally and metabolically more stable than either of the endogenous lipoxins (LXA4 and LXB4). Replacement of the tetraene unit of LXA4 with a benzo-fused ring also allows for efficient synthesis of these analogs. 9,12-LXA4 is a member of this class of benzo-lipoxins and has been shown to have potent anti-inflammatory properties in a mouse model of acute inflammation, significantly reducing polymorphonuclear leukocyte (PMN) infiltration and levels of pro-inflammatory cytokines in vivo (Sun et al. (2009) *Prost. Leuokt. Essent. Fatty Acids* 81:357-366; Petasis et al. (2008) *Bioorg. Med. Chem. Lett.* 18:1382-1387).

In some embodiments, LXA4 analogs can have one of the following structures:

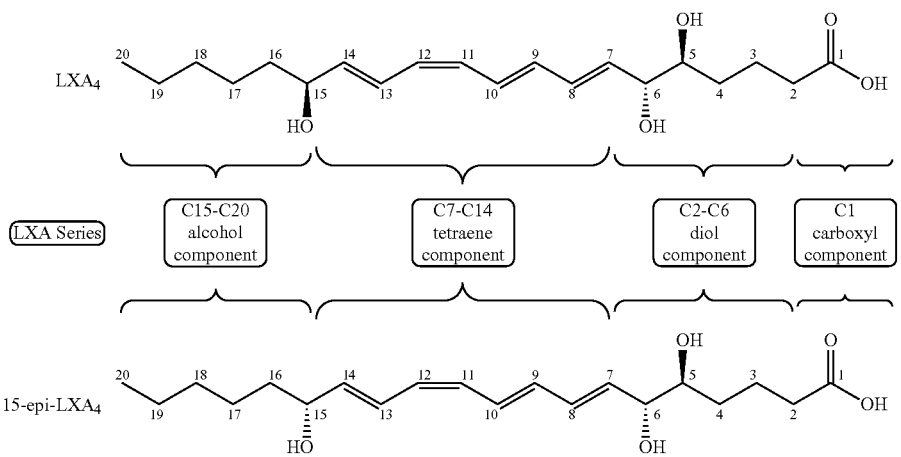 [SMILES: CCCCC[C@H](O)/C=C/C=C\C=C\C=C\[C@@H](O)[C@@H](O)CCCC(=O)O ; CCCCC[C@@H](O)/C=C/C=C\C=C\C=C\[C@@H](O)[C@@H](O)CCCC(=O)O]

These can be expanded to include additional LXA4 analogs having one of the following structures having the designated stereochemistry:

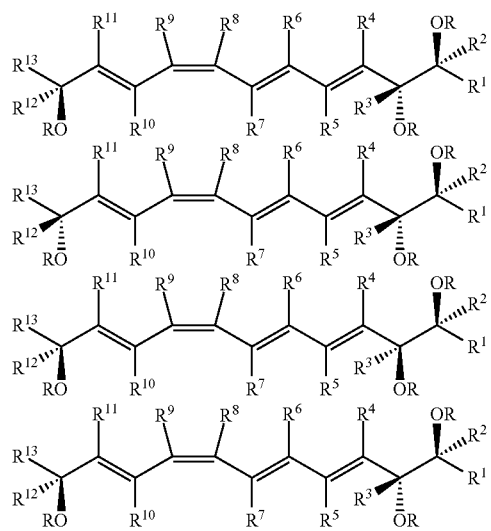

In these structures, the R-groups are independently selected as follows:

R is hydrogen or a straight, branched, cyclic, saturated, or unsaturated alkyl;

$R^1$, $R^2$, $R^{12}$, $R^{13}$ are each independently selected from hydrogen; straight, branched, cyclic, saturated, or unsaturated alkyl having from 1 to 20 carbon atoms; substituted alkyl having from 1 to 20 carbon atoms, wherein the alkyl is substituted with one or more substituents selected from halo, hydroxy, lower alkoxy, aryloxy, amino, alkylamino, dialkylamino, acylamino, acylamino, hydroxyamino, alkoxyamino, alkylthio, arylthio, carboxy, carboxamido, carboalkoxy, aryl, and heteroaryl; substituted aryl or heteroaryl wherein the aryl or heteroaryl is substituted with one or more substituent selected from alkyl, cycloalkyl, alkoxy, halo, aryl, heteroaryl, carboxyl, and carboxamido; and a group Z—Y, wherein Z is a straight, branched, cyclic, saturated, or unsaturated alkyl having from 1 to 20 carbon atoms; substituted lower alkyl wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl wherein the aryl or heteroaryl is substituted with one or more substituents selected from alkyl, cycloalkyl, alkoxy, halo, aryl, heteroaryl, carboxyl, and carboxamido; and Y is selected from hydrogen; alkyl; cycloalkyl; carboxyl; carboxamido; aryl; heteroaryl; substituted aryl or heteroaryl wherein the aryl or heteroaryl is substituted with one or more substituents selected from alkyl, cycloalkyl, alkoxy, halo, aryl, heteroaryl, carboxyl, and carboxamido;

$R^3$ is selected from hydrogen; straight, branched, cyclic, saturated, or unsaturated alkyl having from 1 to 20 carbon atoms; substituted alkyl having from 1 to 20 carbon atoms, wherein the alkyl is substituted with one or more substituents selected from the group consisting of halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido; and $R^4$-$R^{11}$ are selected from a group consisting of: hydrogen; halo; straight, branched, cyclic, saturated, or unsaturated alkyl having from 1 to 20 carbon atoms; substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl wherein the aryl or heteroaryl are substituted with one or more substituent selected from alkyl, cycloalkyl, alkoxy, halo, aryl, heteroaryl, carboxyl, and carboxamido;

R, $R^1$-$R^{13}$ may be also connected to form one or more rings containing 3 to 20 carbon atoms, 1 to 6 oxygen atoms or 1 to 6 nitrogen atoms.

A pair selected among the 1V-$R^{13}$ groups may also be replaced with a bond that generates a carbon-carbon double or triple bond or a ring.

Examples of exemplary, representative LXA4 analogs are shown in Scheme 1. These examples are provided for purposes of illustration and in no way limit the scope of the present invention. Also contemplated as preferred compounds are the compounds shown in Scheme 1 wherein the carbon chains and rings shown in the structures additionally possess substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl.

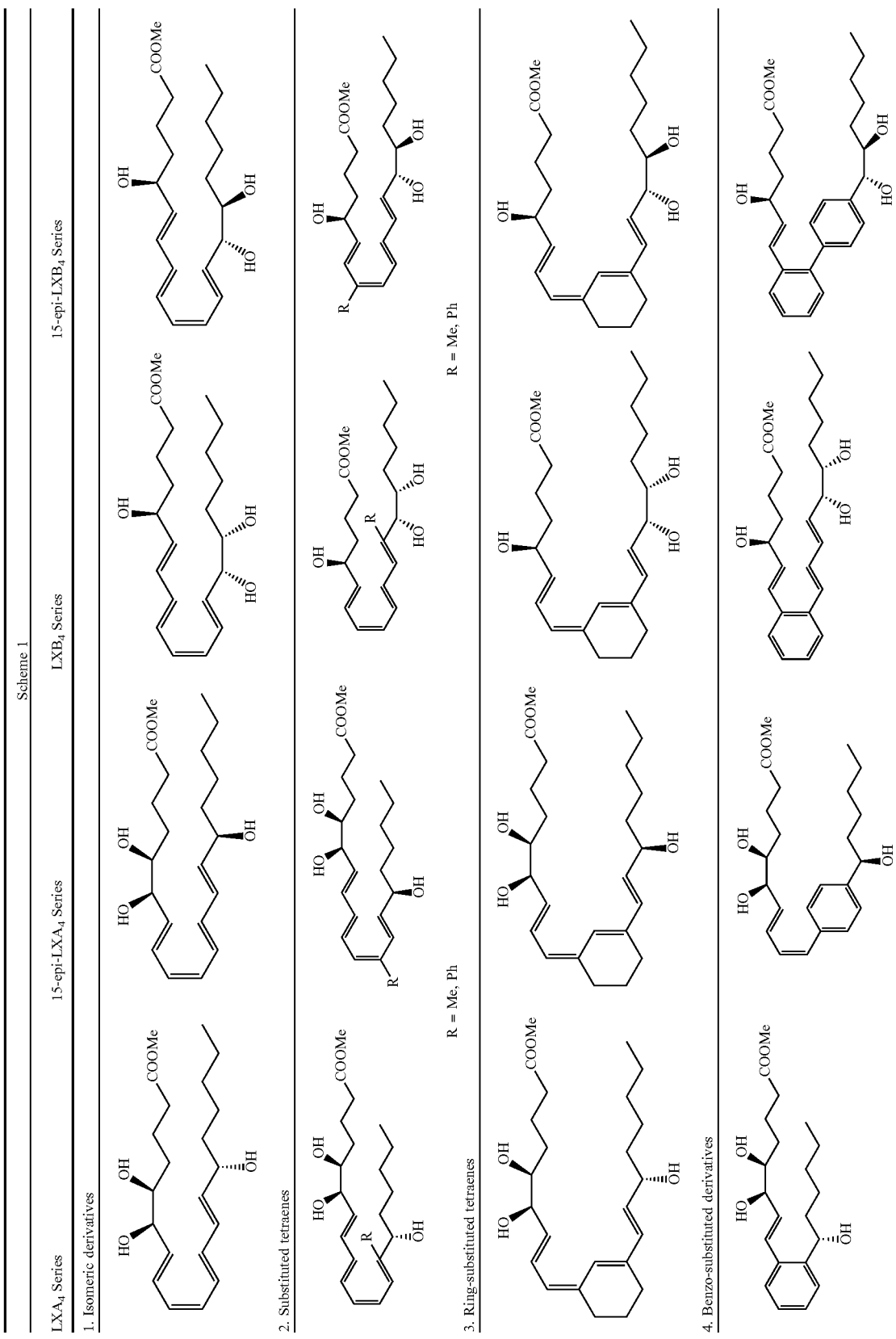
Scheme 1

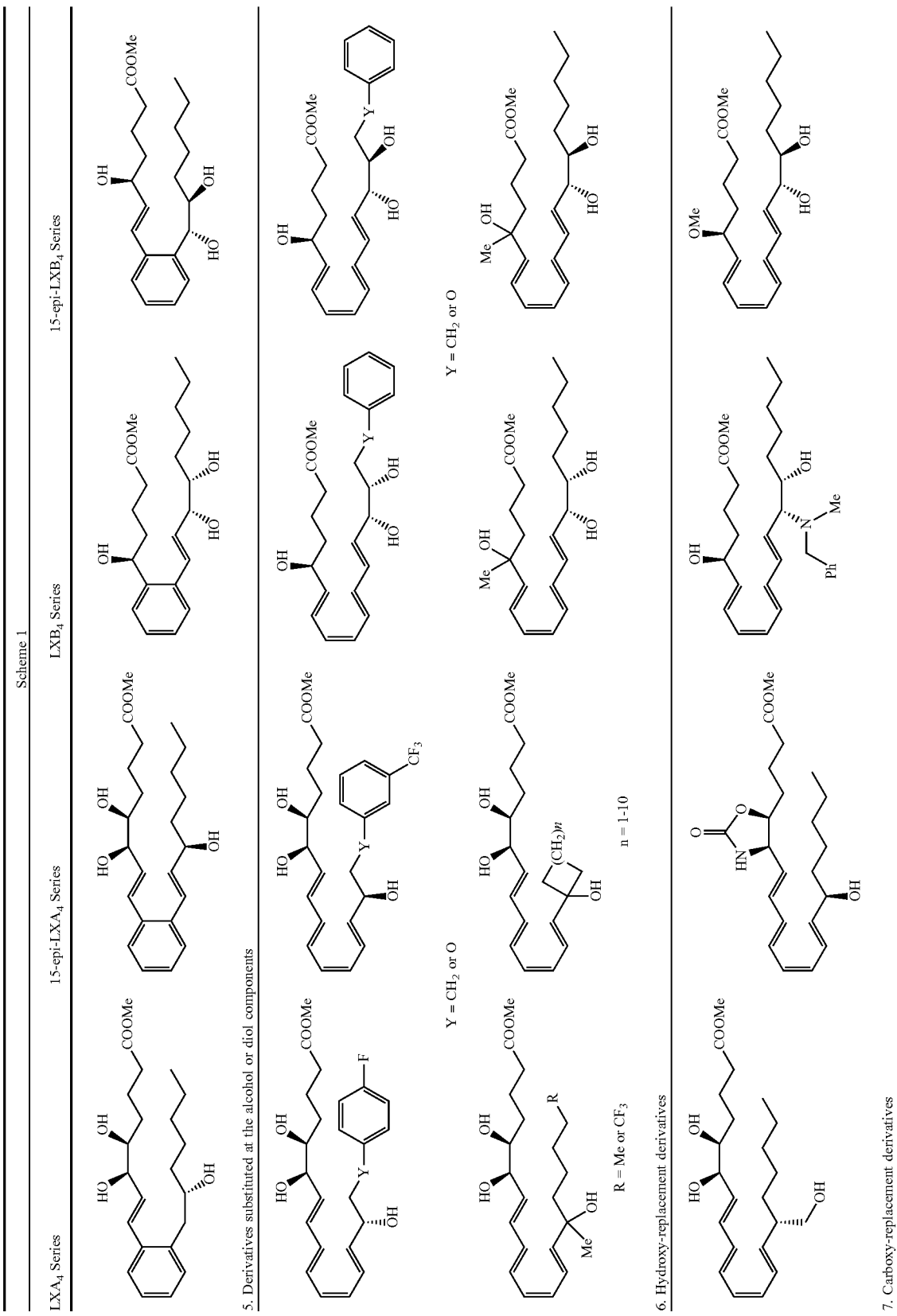

-continued
Scheme 1
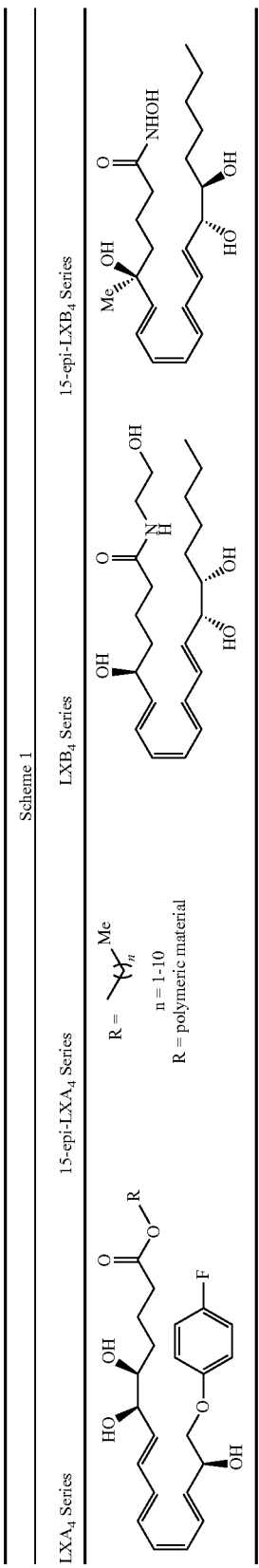

In some embodiments, LXA4 and/or its analogs can be formulated with a physiologically compatible carrier medium. Such media can be of any simple type, e.g., a pharmaceutically acceptable carrier such as fructo-oligo-saccharide (FOS) medium, or other soluble fiber, sugar, nutrient or base material for the composition, with which the LXA4 and/or its analogs can be formulated, e.g., in an orally administrable form. Other non-limiting, exemplary carrier media include mannitol, inulin (a polysaccharide), polydextrose, arabinogalactan, polyolslactulose, lactitol, etc. A wide variety of materials can be used as carrier material in the practice of the present disclosure, as will be apparent to those of ordinary skill in the art, based on the description herein.

The carrier medium, when present, can be blended with LXA4 and/or its analogs in any suitable amounts, such as an amount of from 5% to 95% by weight of carrier medium, based on the total volume or weight of LXA4 and/or its analogs and the carrier medium. In some embodiments, the amount of carrier medium can be in a range having a lower limit of any of 5%, 10%, 12%, 15%, 20%, 25%, 28%, 30%, 40%, 50%, 60%, 70% or 75%, and an upper limit, higher than the lower limit, of any of 20%, 22%, 25%, 28%, 30%, 40%, 50%, 60%, 70%, 75%, 80%, 85%, 90%, and 95%. The amount of carrier medium in a specific embodiment may be determined based on considerations of the specific dose form, relative amounts of LXA4 and/or its analogs, the total weight of the composition including the carrier medium and the bacterial species, and the physical and chemical properties of the carrier medium, and other factors, as known to those of ordinary skill in the LXA4 formulation art.

D. Receptor for Lipid Agonists

Receptors for lipid agonists, such as ERV1, may be any receptor that interacts with any of the Resolvins and lipoxins described in Section B and C supra, where upon interaction or binding to said receptor elicits an anti-inflammatory response. The receptor for Resolvin may be G-protein coupled receptor (GPCR) family that bind either of its agonists, Resolvin RvE1 and the adipokine chemerin) mobilizes intracellular calcium and affects several other signaling cascades within the cell, including NF-κB (see figure below). The receptor—a member of the G protein-coupled receptor (GPCR) family—is found on a variety of different cell types, but is highly expressed by dendritic cells, macrophages, cardiomyocytes, adipocytes, and endothelial cells. When RvE1 binds to ChemR23, leukocyte activation is inhibited presumably through the reduced synthesis and reduced release of pro-inflammatory mediators, in turn leading to the reduced influx of blood-borne cells into the site(s) of inflammation (Flower R J, Perretti M. 2005. Controlling inflammation: a fat chance? J Exp Med. 201(5):671-674). ERV1 is also a G protein-coupled receptor expressed by dendritic cells, NK cells, and macrophages (Wittamer et al., 2003, Parolini et al., 2007).

In some embodiments, the receptor for Resolvin E1 may be RVER1 (also called Chemokine like receptor 1, ERV1, ChemR23, ChemerinR, Dez). In some embodiments, the receptor for Resolvin D1 may be G protein-coupled receptor 32 (GPR32). In other embodiments, the receptor for Resolvin D1 may be the proResolvin mediator annexin A1, known as ALX/FPR2. Other contemplated receptors may include, but not limited to, LO-derived eicosanoid receptors such as LXA4 receptor (ALX) and Leukotriene B4 receptor (BLT).

In some embodiments, at least one Receptor for lipid agonist, e.g. ERV1, is overexpressed in a subject to prevent tumor and cancer development. Overexpression of the Receptor for lipid agonist, e.g. ERV1, may enhance RvE1-induced inflammatory changes at the local environment of cancer. In addition, RvE1 and its application in ERV1-transgenic (TG) animals restore the angiogenic transformation, which is a critical process during the oncogenesis and resolution of inflammation. In some embodiments, overexpression of the Receptor for lipid agonist, e.g. ERV1, may include administering the gene that encodes a Receptor or truncated Receptor polypeptide into a subject for stimulating immune response of the subject or therapeutic treatment of a disease. In other embodiments, overexpression of the Receptor for lipid agonist, e.g. ERV1, may include introducing a nucleic acid configured to express a G-protein coupled receptor (GPCR) into a cell that does not endogenously express the GPCR and contacting the cell with a substance comprising a resolving described supra. Such a cell may be analyzed for reduced cytokine induced activation. In other embodiments, an agent may be added to increased either the transcription or the stability of the Receptor, e.g. ERV1, in a target cell/cell population. In other embodiments, the methods of the present invention may displace chemerin (the other identified ligand for ChemR23), which binds to M1 macrophages expressing the Receptor, a pro-inflammatory response is anticipated. RvE1 may displace chemerin and switch the macrophages into a more pro-resolution phenotype/functional role.

The receptors for lipid agonists may be provided as a vector containing the ERV1. In some embodiments, the receptor can be expressed, isolated, and purified from a host cells, as well as the produced by other known recombinant techniques. The vector may be a phage, plasmid, viral, or retroviral vector. The Receptor polynucleotides may be joined to a vector containing a selectable marker propagation in a host. The Receptor polynucleotide should be operatively linked to an appropriate promoter, as the phage lambda PL promoter, the *E. coli* lac, trp, phoA and tac promoters, the SV40 early and late promoters and promoters of retroviral LTRs. The expression vectors will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated. The expressing vectors will also include one or more promoters. Suitable promoters which may be employed include, but are not limited to, retroviral LTR, the SV40 promoter, adenoviral promoters; heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the (3-actin promoter; and human growth hormone promoters. The promoter also may be the native promoter which controls the genes encoding the polypeptides.

The expression vectors may include at least one selectable marker. Such markers include dihydrofolate reductase, G418, glutamine synthase or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, NSO, COS, 293, and Bowes melanoma cells; and plant cells. Appropriate culture mediums and conditions for the above-described host cells are known in the art.

Gene therapy may be used to deliver a gene of interest, e.g., ERV1, to cells affected with diseases for correction of abnormal conditions. Gene transfer methods of the ERV1 gene for treatment of diseases include tumors/cancers such as cancers in lung, prostate, oesophagus, Pharynx, Colon-rectum, liver-bilary tract, stomach, larynx, pancreas, bladder, breast, colon-rectum, ovary, stomach, womb-leasing, pancreas, lung, liver, lymphoma, leukemia. Gene transfer of the ERV1 gene in accordance with the present invention can be accomplished through many means, including by both viral vectors and by non-viral methods.

E. Pharmaceutical Compositions

In some embodiments, the present invention provides pharmaceutically acceptable compositions which comprise a therapeutically-effective amount of one or more Receptor for lipid agonist, e.g. ERV1, or one or more lipid agonists, e.g. Resolvins described above, formulated together with one or more pharmaceutically acceptable carriers (additives) and/or diluents. In another aspect the compositions can be administered as such or in admixtures with pharmaceutically acceptable carriers and can also be administered in conjunction with other anti-cancer therapies, such as chemotherapeutic agents, scavenger compounds, radiation therapy, biologic therapy, and the like. Conjunctive therapy thus includes sequential, simultaneous and separate, or co-administration of the composition, wherein the therapeutic effects of the first administered has not entirely disappeared when the subsequent compound is administered. In some embodiments, at least one Receptor for lipid agonist, e.g. ERV1, may be provided to the subject alone or in combination with at least one lipid agonist, e.g., Resolvin.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, certain embodiments of the one or more Receptor for lipid agonist, e.g. ERV1, and/or one or more lipid agonists, e.g. Resolvins described above, may contain a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the one or more Receptor for lipid agonist, e.g. ERV1, and/or one or more lipid agonists, e.g. Resolvins described above, may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The one or more Receptor for lipid agonist, e.g. ERV1, and/or one or more lipid agonists, e.g. Resolvins described above, may be formulations suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, a formulation of one or more Receptor for lipid agonist, e.g. ERV1, and/or one or more lipid agonists, e.g. Resolvins described above, can comprise other carriers to allow more stability, to allow more stability, different releasing properties in vivo, targeting to a specific site, or any other desired characteristic that will allow more effective delivery of the one or more Receptor for lipid agonist, e.g. ERV1, and/or one or more lipid agonists, e.g. Resolvins described above, to a subject or a target in a subject, such as, without limitation, liposomes, microspheres, nanospheres, nanoparticles, bubbles, micelle forming agents, e.g., bile acids, and polymeric carriers, e.g., polyesters and polyanhydrides. In certain embodiments, an aforementioned formulation renders orally bioavailable a compound of the present invention.

Liquid dosage formulations of one or more Receptor for lipid agonist, e.g. ERV1, and/or one or more lipid agonists, e.g. Resolvins described above, include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an active ingredient. One or more Receptor for lipid agonist, e.g. ERV1, and/or one or more lipid agonists, e.g. Resolvins described above, may also be administered as a bolus, electuary or paste.

In solid dosage forms (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical or transdermal administration of one or more Receptor for lipid agonist, e.g. ERV1, and/or one or more lipid agonists, e.g. Resolvins described above, include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions suitable for parenteral administration can comprise sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In certain embodiments, the above-described pharmaceutical compositions can be combined with other pharmacologically active compounds ("second active agents") known in the art according to the methods and compositions provided herein. Second active agents can be large molecules (e.g., proteins) or small molecules (e.g., synthetic inorganic, organometallic, or organic molecules). In one embodiment, second active agents independently or synergistically help to treat cancer.

For example, chemotherapeutic agents are anti-cancer agents. The term chemotherapeutic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Further, the following drugs may also be used in combination with an antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons α, β, and γ; hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors; antigenic materials; and prodrugs.

Chemotherapeutic agents for use with the compositions and methods of treatment described herein include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In another embodiment, the composition of the invention may comprise other biologically active substances, including therapeutic drugs or pro-drugs, for example, other chemotherapeutic agents, scavenger compounds, antibiotics, anti-virals, anti-fungals, anti-inflammatories, vasoconstrictors and anticoagulants, antigens useful for cancer vaccine applications or corresponding pro-drugs.

Exemplary scavenger compounds include, but are not limited to thiol-containing compounds such as glutathione, thiourea, and cysteine; alcohols such as mannitol, substituted phenols; quinones, substituted phenols, aryl amines and nitro compounds.

Various forms of the chemotherapeutic agents and/or other biologically active agents may be used. These include, without limitation, such forms as uncharged molecules, molecular complexes, salts, ethers, esters, amides, and the like, which are biologically active.

F. Therapeutic Methods

The present invention further provides novel therapeutic methods of preventing, delaying, reducing, and/or treating a cancer, including a cancerous tumor. In one embodiment, a method for preventing or treating cancer in a subject, the method comprising overexpressing at least one Receptor for a lipid agonist. In one embodiment, a method of treatment comprises administering to a subject (e.g., a subject in need thereof), an effective amount of a Resolvin composition in combination with the Receptor. A subject in need thereof may include, for example, a subject who has been diagnosed with a tumor, including a pre-cancerous tumor, a cancer, or a subject who has been treated, including subjects that have been refractory to the previous treatment.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

The methods of the present invention may be used to treat any cancerous or pre-cancerous tumor. In certain embodiments, the cancerous tumor has a highly glycolytic phenotype. For example, highly glycolytic tumors may be located in a tissue selected from brain, colon, urogenital, lung, renal, prostate, pancreas, liver, esophagus, stomach, hematopoietic, breast, thymus, testis, ovarian, skin, bone marrow and/or uterine tissue. In some embodiments, methods and compositions of the present invention may be used to treat any cancer. Cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The compositions described herein may be delivered by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The terms "systemic administration," "administered systemically," "peripheral administration," and "administered peripherally" as used herein mean the administration of the Resolvin such that it enters the patient's system and, thus, is subject to metabolism and other like processes.

The terms "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

In certain embodiments the pharmaceutical compositions are delivered generally (e.g., via oral or parenteral administration). In certain other embodiments the pharmaceutical compositions are delivered locally through direct injection into a tumor or direct injection into the tumor's blood supply (e.g., arterial or venous blood supply). In some embodiments, the pharmaceutical compositions are delivered by both a general and a local administration. For example, a subject with a tumor may be treated through direct injection of a composition containing a composition described herein into the tumor or the tumor's blood supply in combination with oral administration of a pharmaceutical composition of the present invention. If both local and general administration is used, local administration can occur before, concurrently with and/or after general administration. In certain embodiments, the methods of treatment of the present invention, including treating a cancerous or pre-cancerous tumor comprise administering compositions described herein in combination with a second agent and/or therapy to the subject. By "in combination with" is meant the administration of the one or more Receptor for lipid agonist, e.g. ERV1, and/or one or more lipid agonists, e.g. Resolvins described above, with one or more therapeutic agents either simultaneously, sequentially, or a combination thereof. Therefore, a subject administered a combination of one or more Receptor for lipid agonist, e.g. ERV1, and/or one or more lipid agonists, e.g. Resolvins described above, and/or therapeutic agents, can receive the Resolvin as described herein, and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, 240 mins. or longer of one another. In other embodiments, agents administered sequentially, can be administered within 1, 5, 10, 15, 20 or more days of one another.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

Such methods in certain embodiments comprise administering pharmaceutical compositions comprising compositions described herein in conjunction with one or more chemotherapeutic agents and/or scavenger compounds, including chemotherapeutic agents described herein, as well as other agents known in the art. Conjunctive therapy includes sequential, simultaneous and separate, or co-administration of the composition in a way that the therapeutic effects of the one or more Receptor for lipid agonist, e.g. ERV1, and/or one or more lipid agonists, e.g. Resolvins described above, administered have not entirely disappeared when the subsequent compound is administered. In one embodiment, the second agent is a chemotherapeutic agent. In another embodiment, the second agent is a scavenger compound. In another embodiment, the second agent is radiation therapy. In a further embodiment, radiation therapy may be administered in addition to the composition. In certain embodiments, the second agent may be co-formulated in the separate pharmaceutical composition.

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Dosage may be based on the amount of the one or more Receptor for lipid agonist, e.g. ERV1, and/or one or more lipid agonists, e.g. Resolvins described above, per kg body weight of the patient. For example, a range of amounts of compositions or compound encapsulated therein are contemplated, including about 0.001, 0.01, 0.1, 0.5, 1, 10, 15, 20, 25, 50, 75, 100, 150, 200 or 250 mg or more of such compositions per kg body weight of the patient. Other amounts will be known to those of skill in the art and readily determined.

In certain embodiments, the dosage of the one or more Receptor for lipid agonist, e.g. ERV1, and/or one or more lipid agonists, e.g. Resolvins described above, will generally be in the range of about 0.001 mg to about 250 mg per kg body weight, specifically in the range of about 50 mg to about 200 mg per kg, and more specifically in the range of about 100 mg to about 200 mg per kg. In one embodiment, the dosage is in the range of about 150 mg to about 250 mg per kg. In another embodiment, the dosage is about 200 mg per kg.

In some embodiments the molar concentration of the one or more Receptor for lipid agonist, e.g. ERV1, and/or one or more lipid agonists, e.g. Resolvins described above, in a pharmaceutical composition will be less than or equal to about 2.5 M, 2.4 M, 2.3 M, 2.2 M, 2.1 M, 2 M, 1.9 M, 1.8 M, 1.7 M, 1.6 M, 1.5 M, 1.4 M, 1.3 M, 1.2 M, 1.1 M, 1 M, 0.9 M, 0.8 M, 0.7 M, 0.6 M, 0.5 M, 0.4 M, 0.3 M or 0.2 M. In some embodiments the concentration of the one or more Receptor for lipid agonist, e.g. ERV1, and/or one or more lipid agonists, e.g. Resolvins described above, will be less than or equal to about 0.10 mg/ml, 0.09 mg/ml, 0.08 mg/ml, 0.07 mg/ml, 0.06 mg/ml, 0.05 mg/ml, 0.04 mg/ml, 0.03 mg/ml or 0.02 mg/ml.

Actual dosage levels of the active ingredients in the compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular therapeutic agent in the formulation employed, or the ester, salt or amide thereof, the route of administration, the time of administration, the rate of excretion or metabolism of the particular therapeutic agent being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained.

As described above, the one or more Receptor for lipid agonist, e.g. ERV1, and/or one or more lipid agonists, e.g. Resolvins described above, may be administered in combination with radiation therapy. An optimized dose of radiation therapy may be given to a subject as a daily dose. Optimized daily doses of radiation therapy may be, for example, from about 0.25 to 0.5 Gy, about 0.5 to 1.0 Gy, about 1.0 to 1.5 Gy, about 1.5 to 2.0 Gy, about 2.0 to 2.5 Gy, and about 2.5 to 3.0 Gy. An exemplary daily dose may be, for example, from about 2.0 to 3.0 Gy. A higher dose of radiation may be administered, for example, if a tumor is resistant to lower doses of radiation. High doses of radiation may reach, for example, 4 Gy. Further, the total dose of radiation administered over the course of treatment may, for example, range from about 50 to 200 Gy. In an exemplary embodiment, the total dose of radiation administered over the course of treatment ranges, for example, from about 50 to 80 Gy. In certain embodiments, a dose of radiation may be given over a time interval of, for example, 1, 2, 3, 4, or 5 mins., wherein the amount of time is dependent on the dose rate of the radiation source.

In certain embodiments, a daily dose of optimized radiation may be administered, for example, 4 or 5 days a week, for approximately 4 to 8 weeks. In an alternate embodiment, a daily dose of optimized radiation may be administered daily seven days a week, for approximately 4 to 8 weeks. In certain embodiments, a daily dose of radiation may be given a single dose. Alternately, a daily dose of radiation may be given as a plurality of doses. In a further embodiment, the optimized dose of radiation may be a higher dose of radiation than can be tolerated by the patient on a daily base. As such, high doses of radiation may be administered to a patient, but in a less frequent dosing regimen.

The types of radiation that may be used in cancer treatment are well known in the art and include electron beams, high-energy photons from a linear accelerator or from radioactive sources such as cobalt or cesium, protons, and neutrons. An exemplary ionizing radiation is an x-ray radiation.

Methods of administering radiation are well known in the art. Exemplary methods include, but are not limited to, external beam radiation, internal beam radiation, and radiopharmaceuticals. In external beam radiation, a linear accelerator is used to deliver high-energy x-rays to the area of the body affected by cancer. Since the source of radiation originates outside of the body, external beam radiation can be used to treat large areas of the body with a uniform dose of radiation. Internal radiation therapy, also known as brachytherapy, involves delivery of a high dose of radiation to a specific site in the body. The two main types of internal radiation therapy include interstitial radiation, wherein a source of radiation is placed in the effected tissue, and intracavity radiation, wherein the source of radiation is placed in an internal body cavity a short distance from the affected area. Radioactive material may also be delivered to tumor cells by attachment to tumor-specific antibodies. The radioactive material used in internal radiation therapy is typically contained in a small capsule, pellet, wire, tube, or implant. In contrast, radiopharmaceuticals are unsealed sources of radiation that may be given orally, intravenously or directly into a body cavity.

Radiation therapy may also include stereotactic surgery or stereotactic radiation therapy, wherein a precise amount of radiation can be delivered to a small tumor area using a linear accelerator or gamma knife and three dimensional conformal radiation therapy (3DCRT), which is a computer assisted therapy to map the location of the tumor prior to radiation treatment.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the one or more Receptor for lipid agonist, e.g. ERV1, and/or one or more lipid agonists, e.g. Resolvins described above, described herein relative to the control. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the one or more Receptor for lipid agonist, e.g. ERV1, and/or one or more lipid agonists, e.g. Resolvins described above, described herein relative to control. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the one or more Receptor for lipid agonist, e.g. ERV1, and/or one or more lipid agonists, e.g. Resolvins described above, described herein relative to control. Although compounds that exhibit toxic side effects may be used, care should be taken to design a delivery system that targets the compounds to the desired site in order to reduce side effects.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% inhibition of cancer cell growth in an assay.

In any of the above-described methods, the administering of the one or more Receptor for lipid agonist, e.g. ERV1, and/or one or more lipid agonists, e.g. Resolvins described above, can result in at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy in a subject, compared to the solid malignancy before administration of the Resolvin compositions.

In some embodiments, the therapeutically effective amount of one or more Receptor for lipid agonist, e.g. ERV1, and/or one or more lipid agonists, e.g. Resolvins described above, is administered prophylactically to prevent a solid malignancy from forming in the subject.

In some embodiments, the subject is human. In other embodiments, the subject is non-human, such as a mammal.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ as determined in cell culture. Such information may be used to more accurately determine useful doses in humans. Levels in plasma may be measured, for example, by high performance liquid chromatography.

EXEMPLIFICATION

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

SUMMARY OF EXAMPLES

Background

Inflammation plays a significant role in carcinogenesis and tumor development. Resolvin E1 (RvE1) is an active mediator of resolution of inflammation derived from the n-3 polyunsaturated fatty acid eicosapentaenoic acid (EPA). In this study, we tested the hypothesis that RvE1 and overexpression of the receptor for RvE1 (ERV1) will modify oncogenesis in a xenograft model of lung cancer in mice. Materials and Methods: ERV1-overexpressing transgenic (Tg; n=18) and wild type (Wt; n=18) FVB mice were divided into three experimental groups. All groups received injection of $1 \times 10^6$ LA-P0297 lung cancer cells subcutaneously. The first group served as a no-treatment control. The second group received intraperitoneal 100 ng of RvE1 daily for 6 days and then weekly for 3 weeks. The third group received vehicle. After 4 weeks, animals were sacrificed; tumor tissues and blood were collected for further analyses, including immunohistochemistry, quantitative PCR, and multiplex immunoassay. Results: RvE1 treatment significantly reduced tumor growth in both Wt and Tg animals. Significant necrosis of tumors was observed in Tg mice. Expression of COX-2, NF-κB and production of pro-inflammatory cytokines (G-CSF, IL-1α, IL-6, IL-8, IL-12, TNFα) was significantly reduced with RvE1 treatment (p<0.001) and this decrease was significantly higher in Tg animals. A significant decrease in expression of the tumor marker of Ki67 and angiogenic markers CD34 and CD31 were observed with RvE1 treatment in both Wt and Tg groups (p<0.001); the decrease was significantly greater (p<0.01) in Tg mice, as was VEGF, Ang1 and Ang2 mRNA expression.

Conclusion

Pre-treatment with RvE1 prevents inflammation and vascularization resulting in tumor necrosis. Overexpression of the ERV1 receptor increased the bioavailability and anti-inflammatory activity of RvE1, and increased its impact on tumor seeding and growth.

Example 1: Materials and Methods

Reagents:

RvE1 was purchased from Cayman Chemicals (Ann Arbor, MI). LA-P0297 lung cancer cells were received as a gift from Dr. P. Huang, Massachusetts General Hospital, Boston, MA Ki67, VEGF, CD34 and CD31 primary antibodies were purchased from Abcam (Cambridge, MA). Culture media and TriZol reagent were obtained from Invitrogen (Carlsbad, CA, USA). Primers for NF-κB, COX-2, Ang-1 and Ang-2 were purchased from Life Tech (Grand Island, NY). Milliplex kits for multiplex cytokine analysis were obtained from Millipore (Billerica, MA). An inverted microscope (Zeiss Axiovert 200) from Carl Zeiss Microimaging Inc. (Thornwood, NY, USA) was used for imaging.

Animal Model and Generation of ERV1 Transgenic Mice:

ERV1-transgenic mice (Tg) were engineered as previously described (Gao et al., 2013). In brief, the full-length of hCD11b promoter cDNA was cloned upstream of the full-length chemR23 cDNA (GenBank accession: www.ncbi.nlm.nih.gov/nuccore/NM_004072). For genotyping, genomic DNA was collected from ear punch biopsies of mice and screened by PCR with primers directed to mouse ERV1 (forward primer 5'-CTCGGTCTCCTAGGCAAC-3') and human ERV1 (forward primer 5'-GTCTTCCTCC-CAATCCAT-3'). The mouse and human ERV1 amplicons share the same reverse primer (5'-TAGAAAGCCAGGACCCAG-3'). FVB Wild type female mice (Wt) were purchased from Jackson Laboratories (Bar Harbor, ME). All animals were housed under specific pathogen-free conditions, received standard laboratory chow diet and water ad libitum. All animal experiments were approved by the Institutional Animal Care and Use Committee (IACUC) at the Forsyth Institute and were performed in conformance to the standards of the Public Health Service Policy on Humane Care and Use of Laboratory Animals. The animals were acclimatized before being used in the experimental study.

After one week of acclimatization, all animals received an injection of $1 \times 10^6$ LA-P0297 lung cancer cells subcutaneous in the right flank. Both Wt (n=18) and Tg (n=18) animals were randomly divided into 3 experimental groups: untreated controls; 100 ng of RvE1 diluted in PBS injected intraperitoneal daily for the first 6 days and weekly thereafter for 3 weeks; vehicle, which was 5% ethanol diluted in PBS. RvE1 was stored in 100% ethanol and diluted in PBS immediately before use. RvE1 and vehicle were administered 30 minutes before the injection of cancer cells. Animals were checked routinely for body weight and growth of tumors on the skin. Tumor volume was measured using a Vernier caliper (Mitutoyo, Japan) and calculated using the following formula: $V=\frac{1}{2}(L \times W^2)$ where L=length and W=width. After 28 days, the animals were euthanized by $CO_2$ asphyxia; tumor tissues were collected and stored for histological and molecular analyses.

Histological and Immunohistochemical Analyses:

To examine the microscopic alterations in the tumor tissue, tissues were fixed in 10% formalin, paraffin embedded, sectioned (5 μm) and stained with hematoxylin and eosin. Images were photographed and enlarged for evaluation.

In order to identify tumor cell proliferation and angiogenesis markers, the expression of Ki67 as a marker of proliferation and CD31, CD34 and VEGF as markers of vascularization was analyzed by immunohistochemistry. Briefly, 5 μm thick sections were de-paraffinized and rehydrated with serial alcohol solutions. Antigen retrieval was performed by incubating the sections in 10 mM sodium citrate (pH 6.0) in a microwave oven first for 5 min at 720 W, then 3 min at 450 W and finally 2 min at 180 W. Endogenous peroxidase activity was quenched by incubating the slides with 3% $H_2O_2$ (in methanol) for 20 minutes at 4° C. followed by blocking with 2% BSA for 30 minutes at room temperature. The sections were then incubated with antibodies to Ki67, CD31, CD34 and VEGF (1:100 dilution) overnight at 4° C. in a humidified chamber. Sections were incubated with ABC reagent VACTASTAIN Elite ABC Standard Kit (PK-6100). The immune reactions were visualized using 3,3-diaminobenzidine tetra hydrochloride (DAB). DAB-stained slides were counterstained lightly with hematoxylin. Slides were dehydrated and mounted with Permount for analysis. Images were acquired and analyzed using the Nikon Eclipse 80i microscope (Japan) and Northern Eclipse imaging Elements-D (NIS-D) software. The results are expressed as percent of total positive cells.

Quantitative mRNA Expression of Inflammatory and Angiogenesis Genes:

In order to analyze the impact of RvE1 on inflammation and angiogenesis, the expression of NF-κB, COX-2, VEGF, Ang-1 and Ang-2 was examined by quantitative real-time PCR. Total cellular RNA was extracted from tumor tissue (stored in RNAlater solution) using TriZol reagent. Quantification of RNA was determined using NanoDrop 1000 (Thermo Fisher Scientific, Wilmington, DE). RNA samples were stored at −80° C. until use. The first-strand cDNA was synthesized with High Capacity cDNA Archive kit (Applied Biosystems, Foster City, CA, USA) according to the manufacturer's instructions. For quantitative RT-PCR analysis, oligonucleotides for NF-κB, COX-2, VEGF, Ang-1, Ang-2 and GAPDH were chosen from predesigned assays. Thermal cycling included initial steps at 50° C. for 2 min and at 95° C. for 10 min, followed by 40 cycles at 95° C. for 15 s and at 60° C. for 1 min. The fluorescence of the double-stranded products was monitored in real time. The cDNA was amplified and quantified using Sequence Detection System (SDS) 7000 (Applied Biosystems). The $2^{(\Delta\Delta Ct)}$ (Ct value of target gene minus Ct value of housekeeping gene) method was used to calculate relative quantity fold-change. GAPDH was used as the housekeeping gene. The data is from 3 independent experiments performed in triplicate.

Quantification of Inflammatory Cytokines:

Inflammation is driven by soluble factors that are produced by tumor cells and by the cells recruited to the tumor microenvironment. Hence, inflammatory cytokines were analyzed in the tumor tissue. Cytokine levels were measured using a multiplex bead array assay kit for Luminex purchased from Millipore to measure the following cytokines: G-CSF, IL-10, IL-6, IL-8, IL-12, TNF ☐, as per the manufacturer's instructions using a Luminex 100 instrument. Appropriate dilutions of the samples in assay diluent were made as required. Each sample was assayed in duplicate and cytokine standards supplied by the manufacturer were used to calculate the concentrations in the samples. Cytokine levels are expressed in pg/ml.

Statistical Analysis:

The results are expressed as mean±SEM. The differences between the groups were assessed by ANOVA after ascertaining normality by Q-Q plot. Statistical significance was determined by one-way ANOVA with Bonferroni's multiple comparison post hoc tests, and differences were considered significant at $p<0.05$.

Example 2: RvE1 Reduces Tumor Size

Animals were monitored every day. None of the animals exhibited any signs of toxicity in response to RvE1 as determined by behavioral changes, eating, drinking habits and movement. Table 1 summarizes the gross clinical observations. All animals in both Wt and Tg groups developed tumors. Vehicle application did not make any difference in the incidence of tumor development. RvE1 pretreatment reduced the number of mice developing tumors to 4 of 6 Wt mice and 3 of 6 Tg mice. One animal in the vehicle treated Wt group developed metastases. There was no significant difference in body weight of Wt and Tg mice with or without RvE1 injection.

TABLE 1

Effect of RvE1 on gross morphological changes

| Groups | Total | Complications | Tumor developed | No tumor | Necrosis | Metastasis |
|---|---|---|---|---|---|---|
| Wt | | | | | | |
| Control | 6 | — | 6 | — | — | — |
| RvE1 | 6 | 2 animals very weak | 4 | Weak animals did not get any tumors | Started on 18$^{th}$ day | — |
| Vehicle | 6 | — | 6 | — | — | 1 |
| Tg | | | | | | |
| Control | 6 | — | 6 | — | — | — |
| RvE1 | 6 | — | 3 | 3 | Started on 18$^{th}$ day | — |
| Vehicle | 6 | — | 6 | — | — | — |

Tumor volume is a simple way to assess the progression of tumor; therefore, we calculated tumor volume to analyze the chemopreventive impact of RvE1 in both Wt and Tg mice. We observed significant morphological differences between Wt and Tg groups with or without RvE1 pretreatment at the macroscopic level (FIG. 1A). The progression of tumor development was significantly ($p<0.001$) reduced in Tg animals as compared to Wt. In response to pretreatment with RvE1, tumor size was reduced significantly ($p<0.001$) in both Wt and Tg animals compared to vehicle and control groups (FIG. 1B). Progression of tumor was exponential from day 7 in control Wt and day 11 in control Tg mice suggesting a delay in progression in Tg animals suggesting a response to endogenously produced RvE1. From 19$^{th}$ day, necrosis was seen on the surface of tumors in the RvE1 treated groups. Tumors of mice receiving RvE1 appeared very soft and pulpous compared to tumors from animals not treated with RvE1, which were solid and rigid (FIG. 1A).

Example 3: Histopathological Analysis of Tumor Tissue in Response to RvE1

Figure 2:
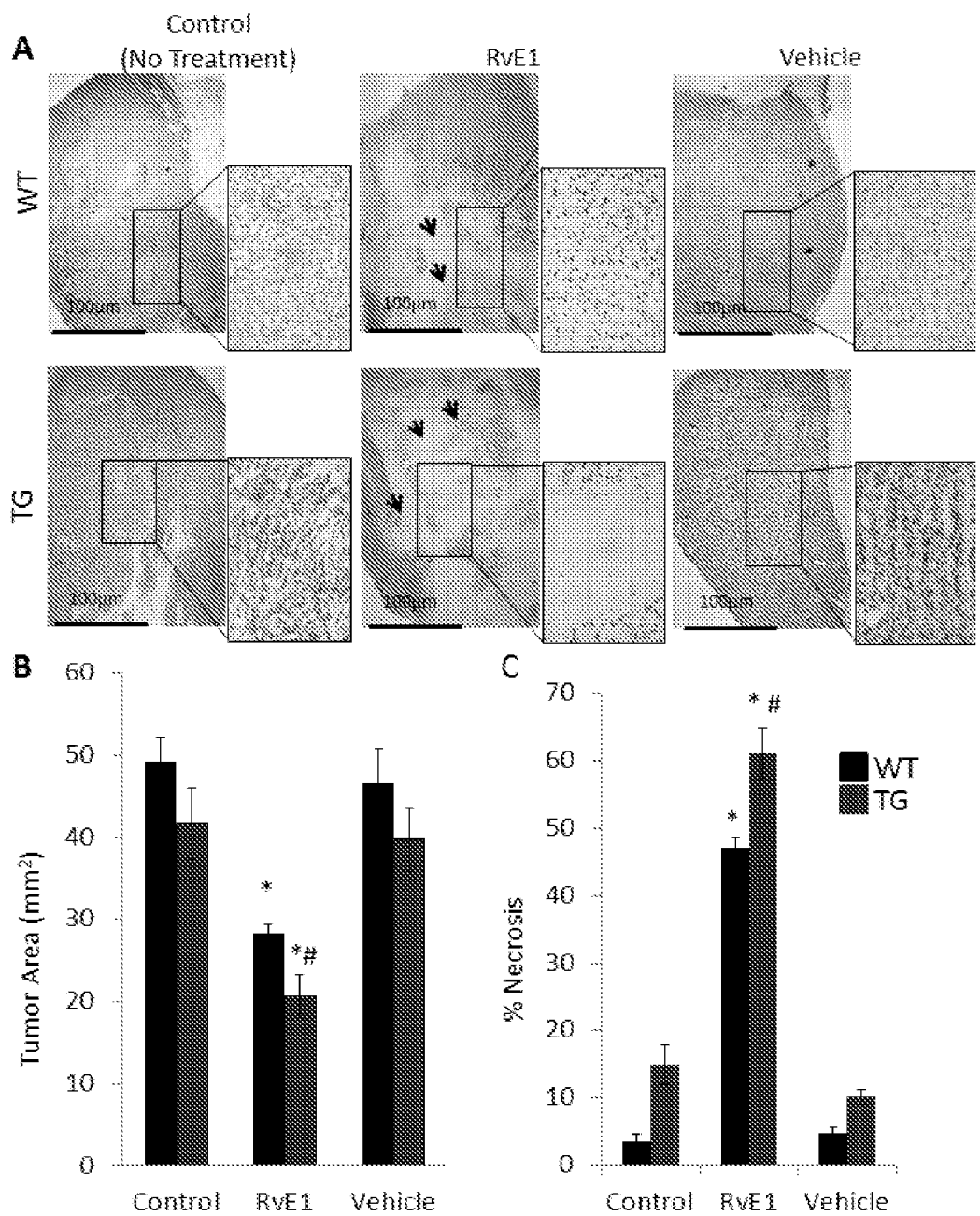
FIG. 2 depicts the impact of RvE1 on microscopical alterations in tumor tissues of Wt and Tg mice ***$p<0.001$ as compared to Wt Control, $^{III}p<0.001$ as compared to Tg Control, $^{¥¥¥}0.001$ as compared to Wt RvE1, $^{¥}p<0.05$ as compared to Wt RvE1. Arrow represents necrosis in the tumor.

Microscopic analyses of the tumor tissues revealed that tumor architecture was intact and clear in the Wt control group (FIG. 2A). Cells formed a tumor nest marked by blood supply. Lymphatic and vascular invasion was present in control samples. Tumor cells showed nucleolus cleavage and high extent of malignancy. Similar architecture was observed in Tg animals in the control group (FIG. 2D). Vehicle treatment did not have any impact on the microscopic architecture of the tumors (FIGS. 2C and 2F). Tumors in RvE1-treated animals showed a central area with reduced staining of the tissue and patches of destroyed tumor indicative of extensive necrosis (FIGS. 2B and 2E). Necrosis was more prominent in RvE1 treated Tg mice compared Wt mice.

Example 4: Inhibition of Cell Proliferation by RvE1 in Tumor Tissue

Figure 3:
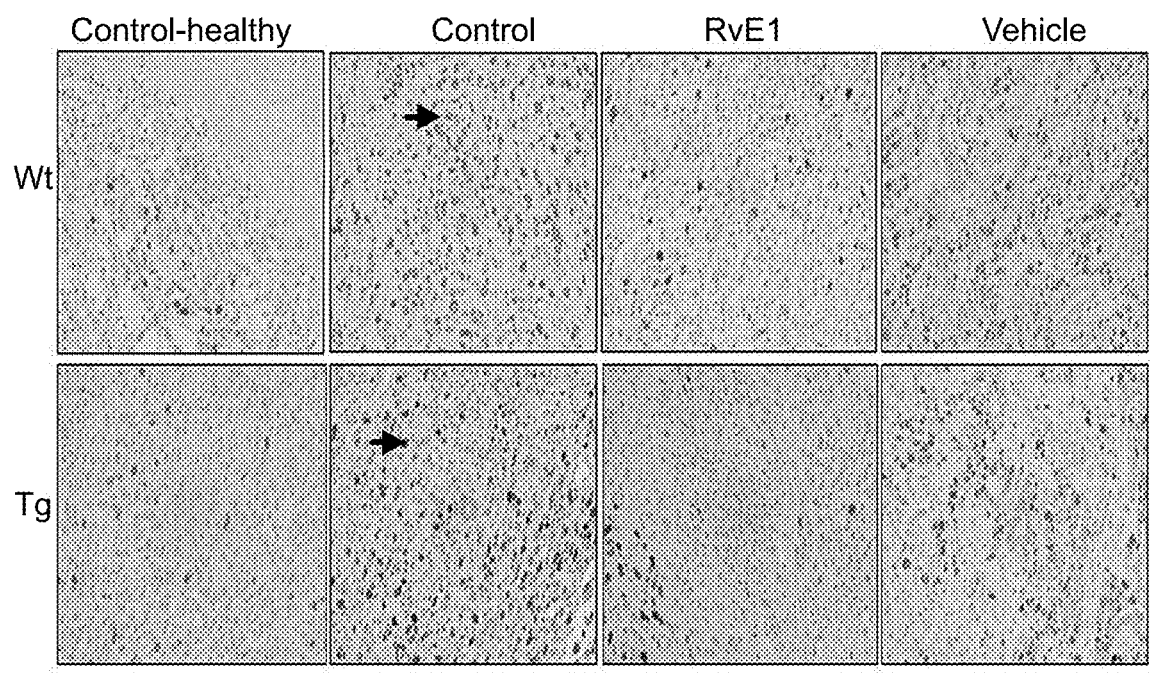
FIG. 3 depicts expression of Ki67 in tumor tissue on pre-treatment of RvE1 A) Representative IHC images for Ki67 in tumor tissue B) quantification of Ki67***$p<0.001$ as compared to Wt Control, $^{III}p<0.001$ as compared to Tg Control, $^{¥¥}p<0.01$ as compared to Wt RvE1. Arrow represents Ki67 positive cells.
Figure 3:
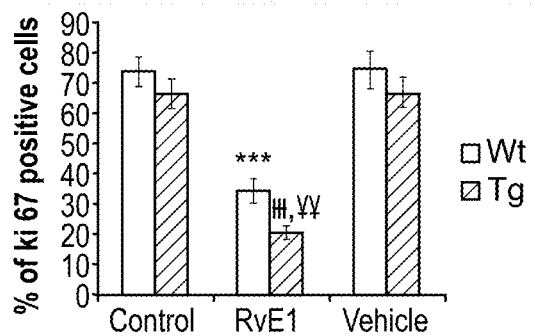

Ki67 protein was used as a marker for cellular proliferation. Ki67 is associated with active phases of the cell cycle and is absent from resting cells. FIG. 3 shows Ki67 expression in cancer tissues. The percentage of Ki67-positive cells was 73.5% and 66% in Wt and Tg control animals, respectively. RvE1 treatment resulted in a significant ($p<0.001$) reduction of Ki67-positive cells in both Wt and Tg groups compared to both vehicle and control groups. The reduction in the expression of Ki67 was significantly (p<0.01) higher in RvE1 treated Tg mice compared to Wt mice treated with RvE1.

Example 5: Modulation of Cytokine Levels with RvE1

Figure 5:
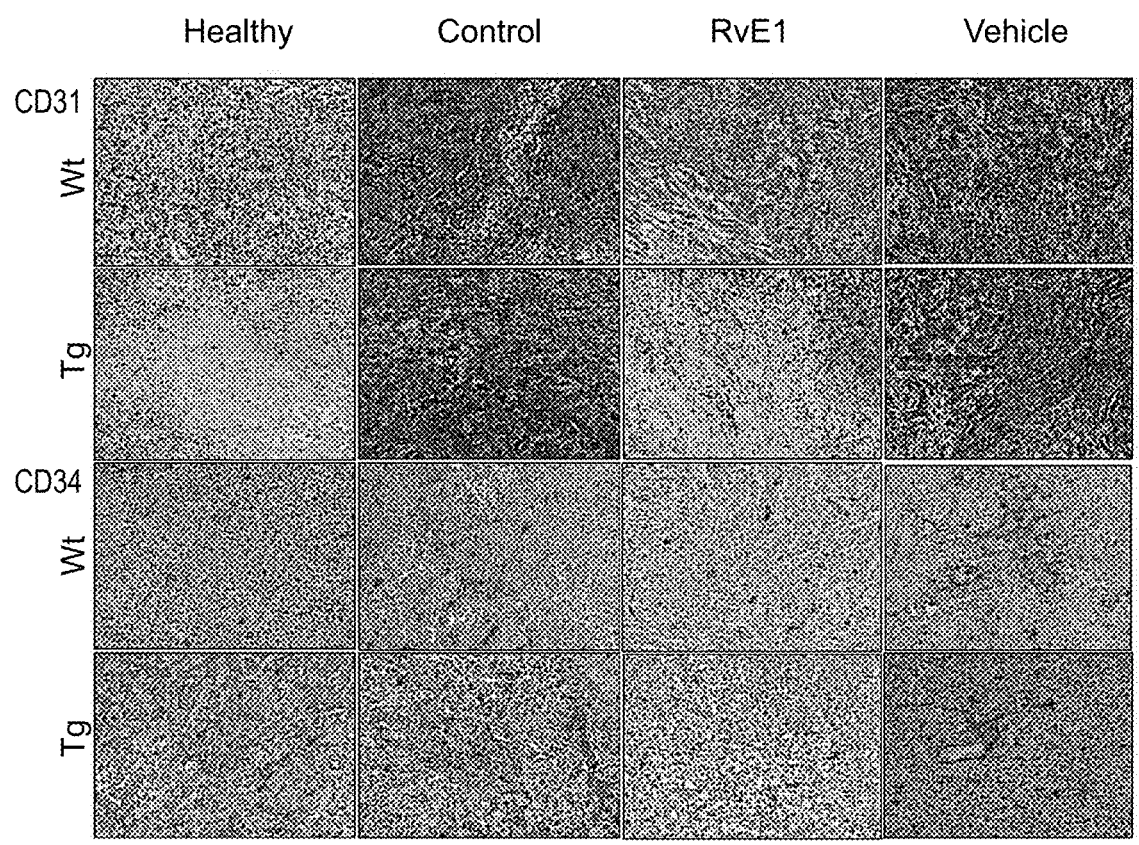
FIG. 5 depicts RvE1 pre-treatment downregulates CD34 and CD31 in tumor tissues of both Wt and Tg mice. CD31, also known as platelet-endothelial cell adhesion molecule-1 (PECAM-1), is a transmembrane glycoprotein adhesion molecule expressed by platelets, and endothelial cells. CD34 is a cell-surface marker expressed in endothelial cells and hematopoietic stem cells. Quantification of CD34 and Cd31 in tumor tissue of both Wt and Tg mice. ***$p<0.001$ as compared to Wt Control, $^{III}p<0.001$ as compared to Tg Control, $^{¥¥}p<0.01$ as compared to Wt RvE1.
Figure 5:
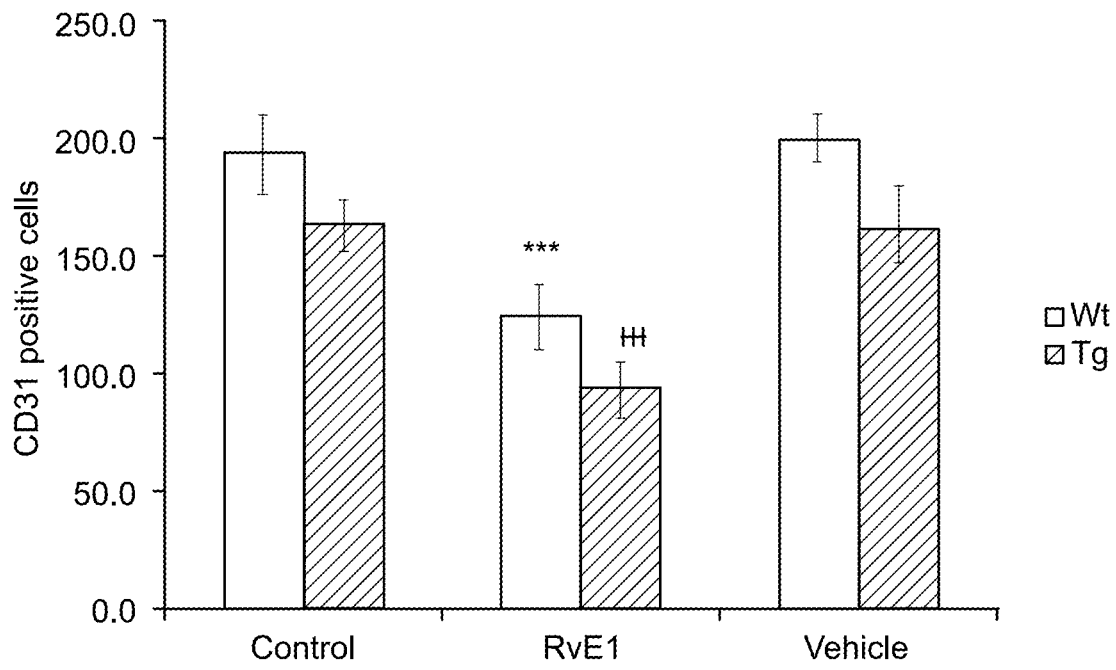
Figure 5:
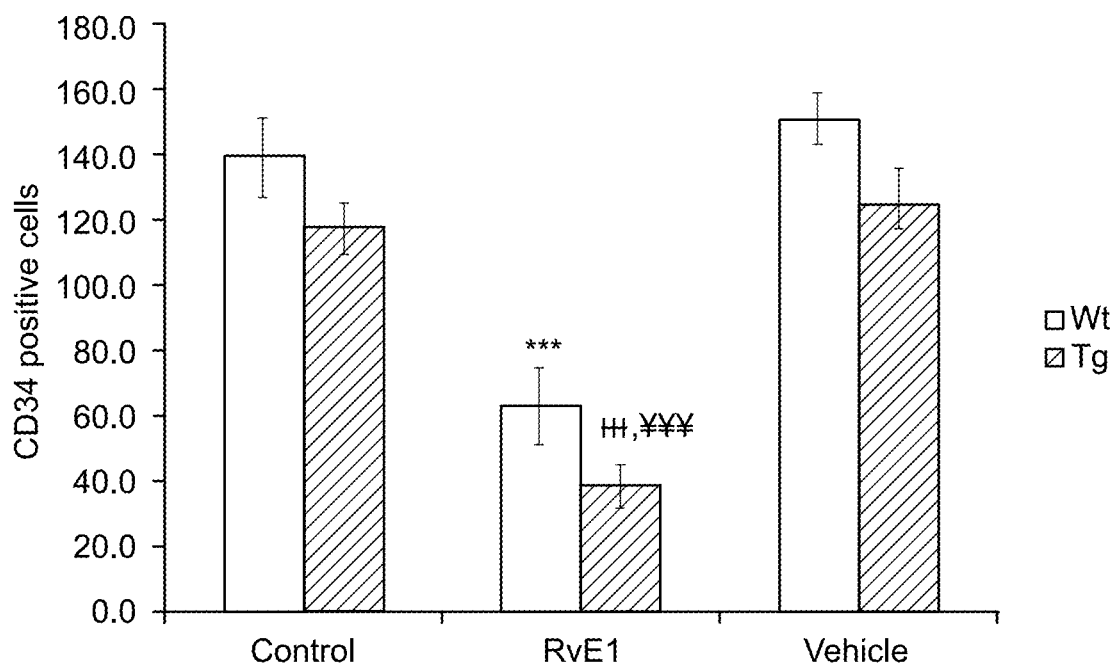

RvE1 treatment resulted in a significant decrease in the levels of pro-inflammatory cytokines (G-CSF, IL-1α, IL-6, IL-8 and IL-12) compared to control and vehicle mice in both Wt and Tg (Table 2). The levels of TNF-α decreased in response to pre-treatment with RvE1 in both Wt and Tg animals, although the reduction was significant only in Tg RvE1 treated mice as compared to Tg control.

did not impact the expression of CD31 and CD34. Intensity was significantly reduced in both Wt and Tg mice in response to RvE1. CD31 and CD34 positive cells were significantly (p<0.001) reduced in response to pretreatment with RvE1 in both the Wt and Tg mice as compared to their respective controls and vehicle groups (FIG. 5). RvE1 reduced the expression of CD34 in tumor tissues in Tg animals significantly more than the Wt animals (p<0.01).

Figure 6:
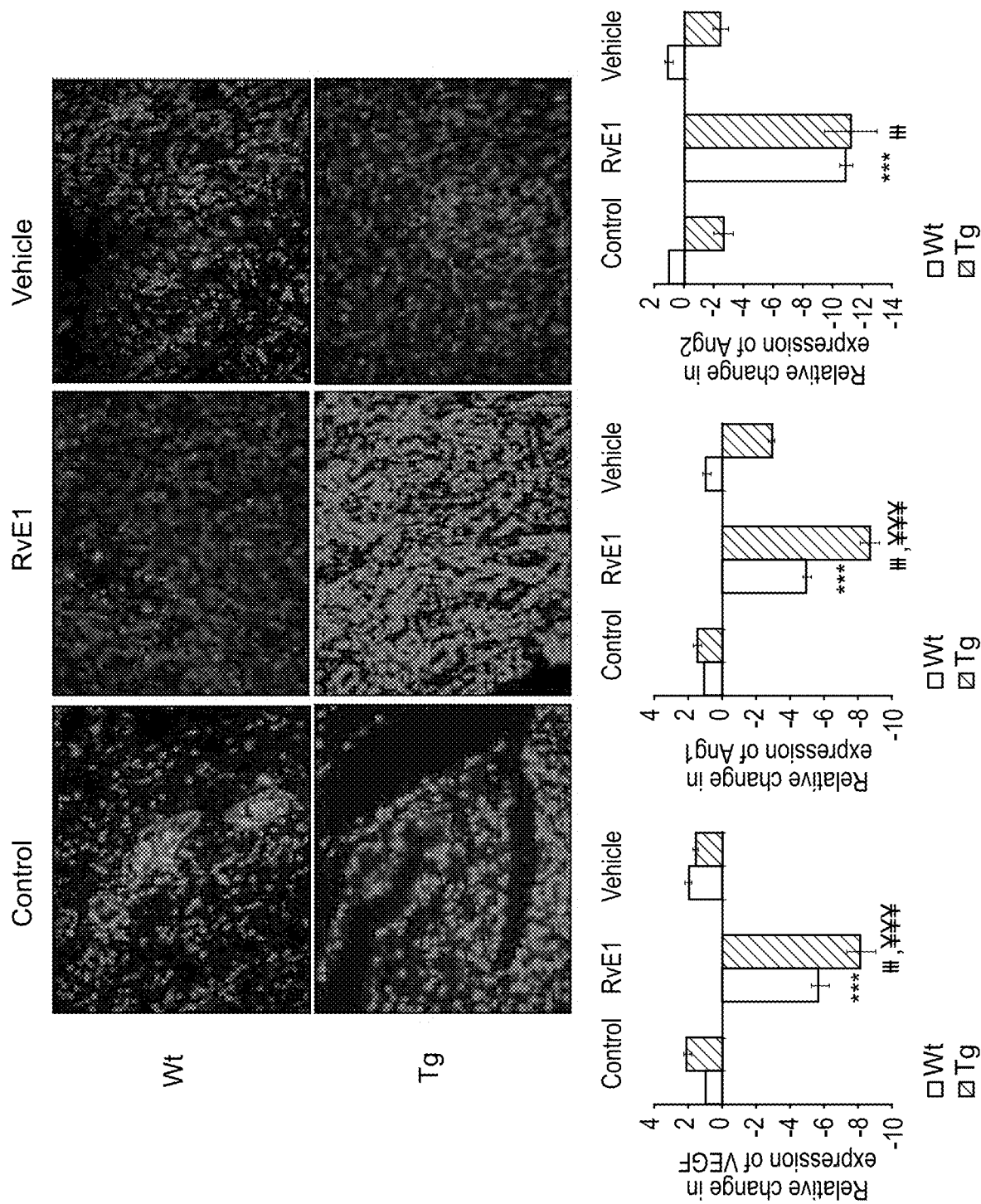
FIG. 6 depicts expression of VEGF, Ang1 and Ang2 in tumor tissue with RvE1 pre-treatment. ***$p<0.001$ as compared to Wt Control, $^{III}p<0.001$ as compared to Tg Control, $^{¥¥¥}p<0.001$ as compared to Wt RvE1.
Figure 7:
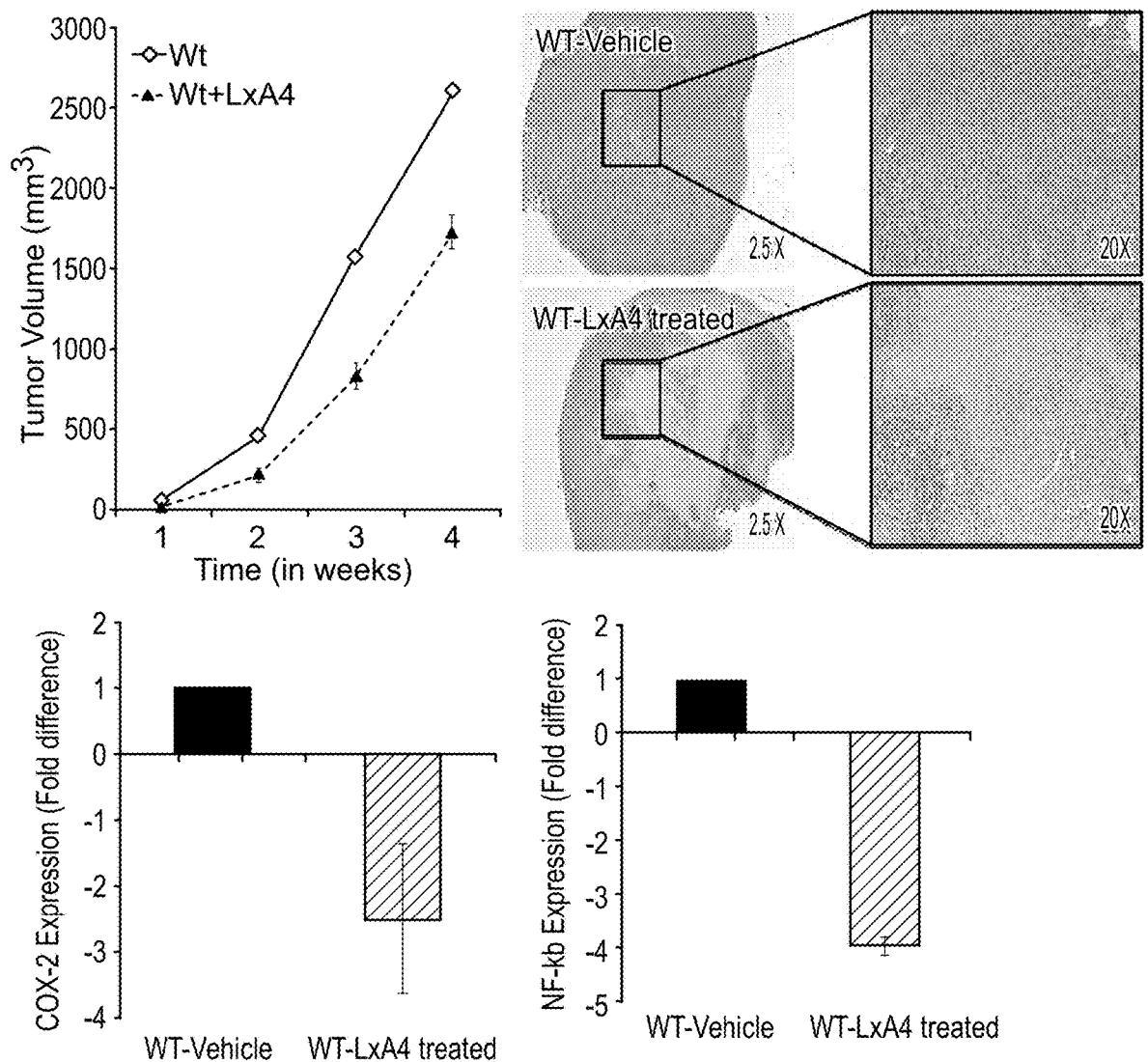
FIG. 7 depicts LXA4 and xenograft model of lung cancer. No change in body weight and difference between groups. LXA4 reduced the tumor volume significantly compared to the vehicle group over a span of 4 weeks (top, right). Center of the tumor tissue was highly necrotic in LXA4-treated group compared to WT-vehicle control where no sign of necrosis was observed over 4 weeks (top, left). Likewise, no sign of inflammatory infiltration was observed in LXA4 group compared to the vehicle in which extensive infiltration of inflammatory cells was observed. In parallel, COX-2 (bottom, left) and NF-Kb (bottom, right) expression were significantly decreased in LXA4-treatment group.
Figure 8:
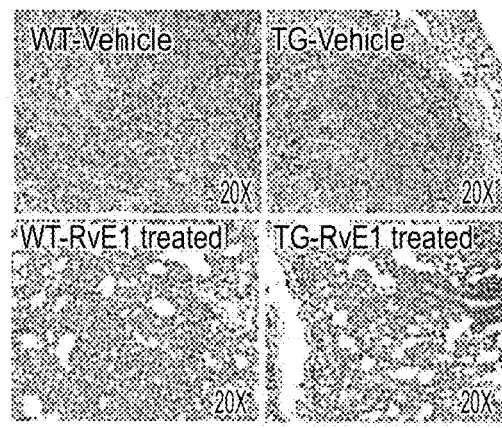
FIG. 8 shows impact of RvE1 on an orthotopic model of lung cancer. Table 2 shows survival over 2 weeks: WT control: 25%, TG control: 25%, WT+RvE1: 40%, and TG+RvE1: 80%; and number of nodules in the lung over 2 weeks: WT control: 8-10 nodules, TG control: 8-10 nodules, WT+RvE1: 4-6 nodules, TG+RvE1: 3-5 nodules. The histological findings indicate intact tumor tissues in lungs from control groups. RvE1 resulted in decreased tumor density, vascularization, and inflammatory infiltration with increased necrosis. COX-2 (bottom, left) and NF-Kb (bottom, right) expression were decreased in TG animals compared to WT animals. RvE1 reduced the expression of COX2 by 6-fold in both groups while 6-7-fold only in the TG animals.
Figure 8:
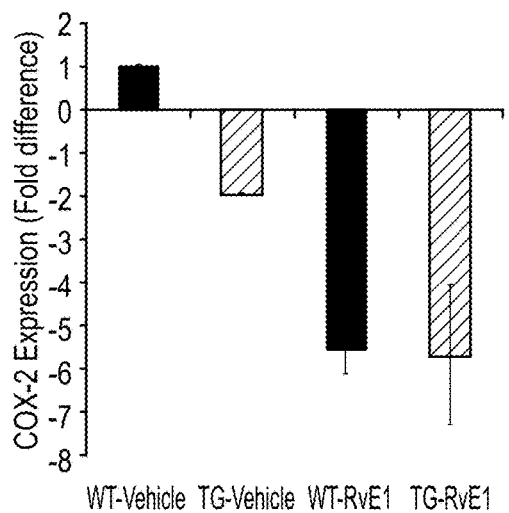
Figure 8:
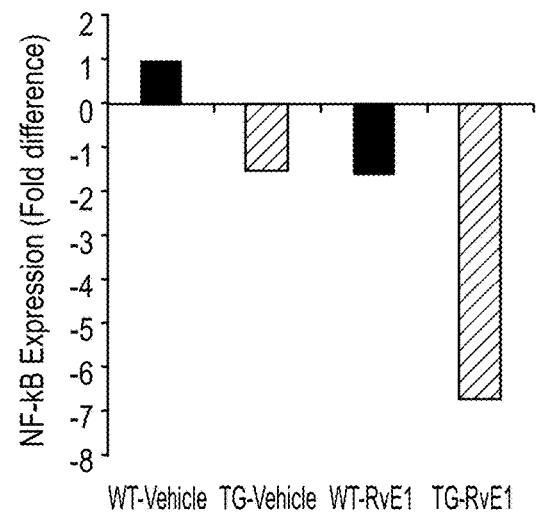
Figure 9:
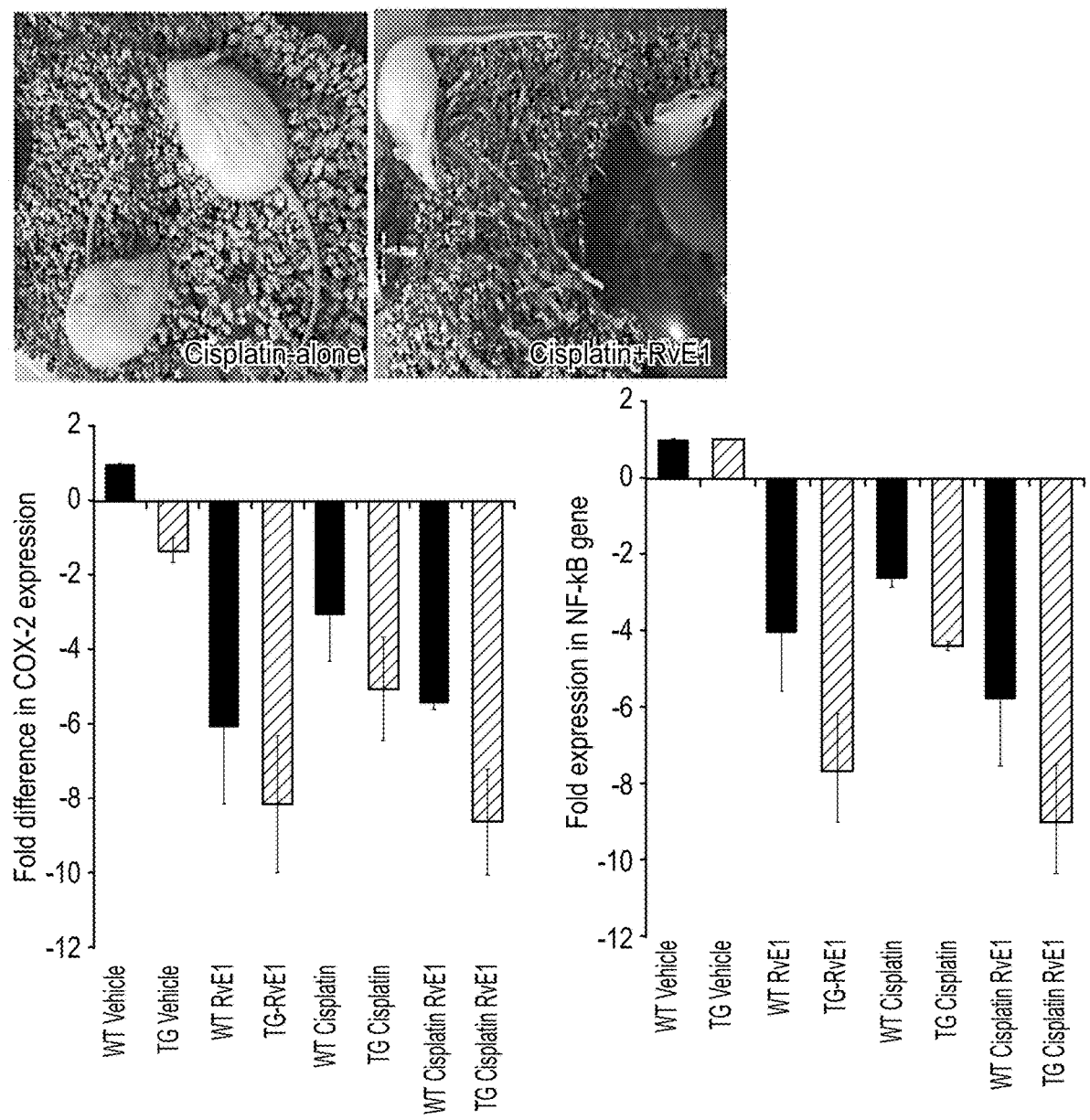
FIG. 9 shows synergistic impact of RvE1 and cisplatin in xenograft model of lung cancer. Animals treated with cisplatin and RvE1 looked healthier and normal in size and behavior compared to animals treated with cisplatin alone. TG animals treated with both RvE1 and cisplatin kept their body weight while cisplatin alone and WT animals lost weight over 4 weeks. Cisplatin reduced the tumor volume. TG animals treated with additional RvE1 showed the least tumor volume over 4 weeks compared to the non-treated and WT groups. Reduction in COX-2 (bottom, left) and NF-Kb (bottom, right) expression was significantly higher in RvE1+Cisplatin treated groups compared to the cisplatin alone. This impact was significantly higher in TG groups compared to the WT groups.

The expression of VEGF was significantly reduced by 5-fold and 7-fold in both Wt and Tg mice, respectively as compared to control and vehicle animals in response to RvE1 (FIG. 6; p<0.001). The decrease was more significant in Tg mice compared to Wt mice treated with RvE1 (p<0.001). In parallel, Ang1 and Ang2 were significantly decreased in the animals treated with RvE1 in both Wt and

TABLE 2

Alteration in cytokines levels in tumor tissue on pre-treatment with RvE1

| | Wt | | | Tg | | |
|---|---|---|---|---|---|---|
| | Control | RvE1 | Vehicle | Control | RvE1 | Vehicle |
| G-CSF | 2494.61 ± 248.9 | 1624.28 ± 170.8** | 2581.94 ± 191.5 | 2110.50 ± 170.6 | 1156.31 ± 145.3 [H] | 2029.31 ± 220.3 |
| IL-1α | 249.16 ± 17.1 | 177.94 ± 15.7* | 234.07 ± 15.3 | 225.58 ± 29.5 | 146.37 ± 32.4 [I] | 225.58 ± 36.7 |
| IL-6 | 185.96 ± 29.2 | 52.06 ± 12.9*** | 200.43 ± 9.1 | 186.74 ± 22.2 | 62.18 ± 3.1 [HH] | 192.70 ± 21.1 |
| IL-12 | 62.24 ± 3.2 | 46.73 ± 4.7* | 63.61 ± 7.4 | 52.82 ± 3.7 | 38.58 ± 2.7 [I] | 52.90 ± 8.3 |
| IL-8 | 3248.60 ± 193.6 | 2629.41 ± 263.3* | 3476.74 ± 344.9 | 2643.93 ± 191.7 | 692.61 ± 101.1 [HH][YYY] | 2910.35 ± 216.3 |
| TNF-α | 17.58 ± 1.7 | 13.23 ± 0.9 | 15.56 ± 1.7 | 17.39 ± 2.1 | 10.06 ± 2.1 [YY] | 17.18 ± 1.8 |

***p < 0.001 as compared to Wt Control,
**p < 0.01 as compared to Wt Control,
*p < 0.05 as compared to Wt Control,
[HH] p < 0.001 as compared to Tg Control,
[H] p < 0.01 as compared to Tg Control,
[I] p < 0.05 as compared to Tg Control,
[YYY] p< 0.001 as as compared to Wt RvE1,
[YY] p < 0.01 as compared to Wt RvE1.

Figure 4:
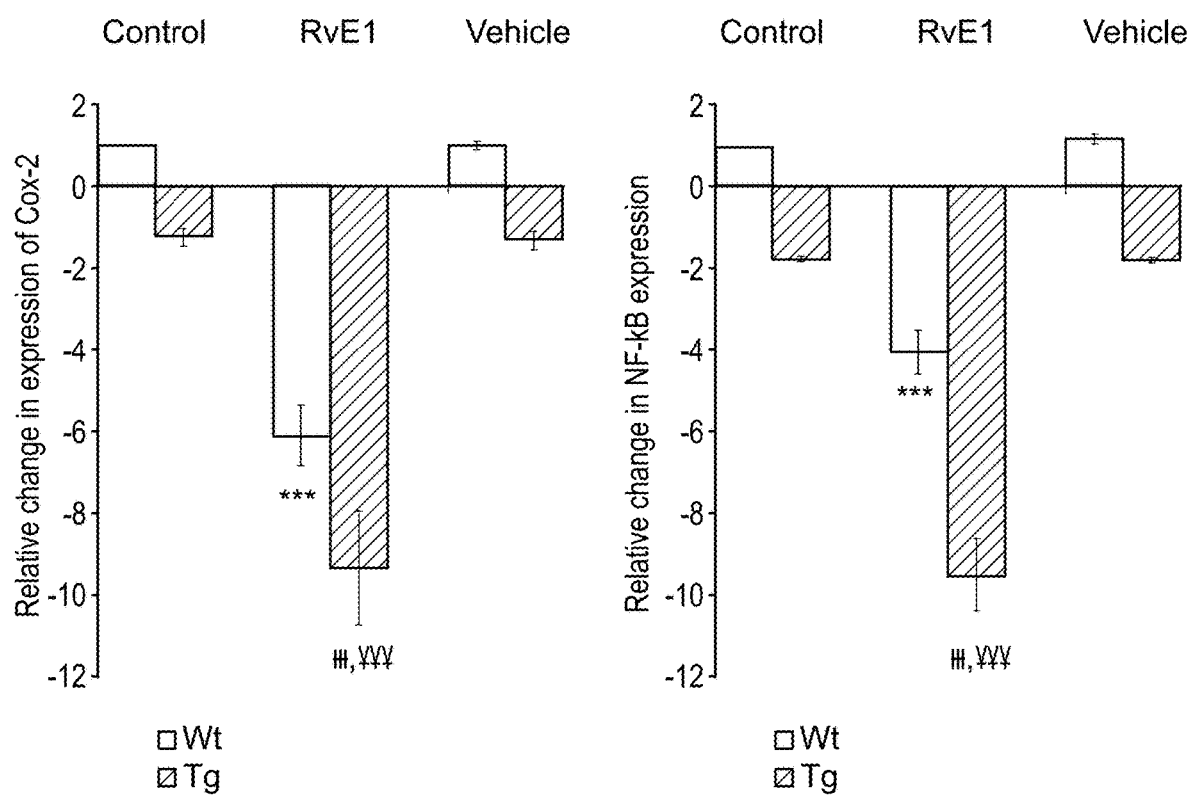
FIG. 4 depicts expression of COX-2 and NF-κB on RvE1 pre-treatment in tumor tissue. ***$p<0.001$ as compared to Wt Control, $^{III}p<0.001$ as compared to Tg Control, $^{¥¥¥}p<0.001$ as compared to Wt RvE1.

Example 6: RvE1 Pre-Treatment Suppresses the Expression of Inflammatory Genes in Tumor Tissue Since RvE1 had an impact on inflammatory cytokines in cancer tissues; we then examined the expression of mRNA for inflammatory molecules and targeted COX-2 and NF-κB in tumor tissues using qPCR (FIG. 4). COX-2 was significantly decreased by 6-fold in Wt mice and 8-fold in Tg mice in response to treatment with RvE1 as compared to their controls and vehicle groups (p<0.001). Likewise, the expression of NF-κB was significantly reduced by 4-fold in Wt mice and 7.6-fold in Tg mice as compared to control and vehicle animals in response to RvE1 (p<0.001).

Example 7: Down-Regulation of Vascularization and Angiogenesis Markers with RvE1

In order to assess whether RvE1 has an impact on vascularization, the expression of CD31 and CD34, was measured by immunohistochemistry. VEGF expression was analyzed by both immunohistochemistry and PCR. Ang1 and Ang2 were evaluated by qPCR. Intensity of staining for CD31 and CD34 was significantly increased in tumors of Wt and Tg animals in control groups compared to the healthy tissues from the same animals (FIG. 5). Vehicle treatment Tg mice compared to the controls and vehicle groups (p<0.001). The decrease in Ang1 expression was more significant in Tg mice compared to the Wt animals (p<0.001).

Figure 10:
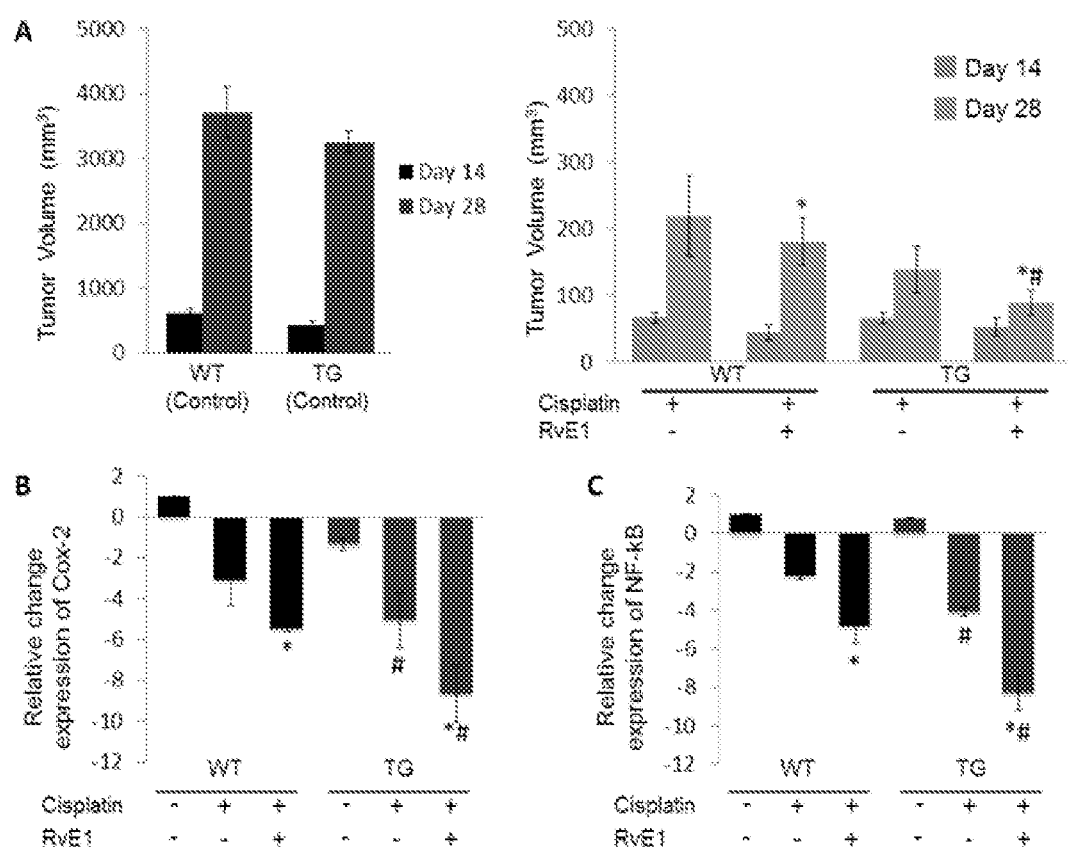
FIG. 10 shows that adjunctive RvE1 reduces tumor size, number and increases the efficacy of cisplatin.

Example 8: Adjunctive RvE1 Reduces Tumor Size, Number and Increases the Efficacy of Cisplatin Animals treated with RvE1+cisplatin looked healthier with no weight loss and problems with behavior. These animals were active compared to animals treated with cisplatin-alone. TG animals treated with RvE1+cisplatin maintained body weight, while the cisplatin-alone group and WT animals lost weight after the first 2 weeks. Cisplatin reduced tumor volume; TG animals treated with additional RvE1 showed markedly reduced tumor volume compared to the non-treated and WT groups. None of the animals exhibited any signs of toxicity in response to RvE1 as determined by behavioral changes; eating, drinking habits and movement. Reduction in COX-2 and NF-κB expression was significantly higher in RvE1+cisplatin treated animals compared to cisplatin alone. The impact was significantly higher in TG groups compared to the WT groups (FIG. 10).

DISCUSSION

Experimental studies have shown that inflammation plays a significant role in the microenvironment of carcinogenesis as a modifying factor through cellular and molecular mechanisms (Hanahan and Weinberg, 2011, Maeda and Omata, 2008). In the present study, it was demonstrated that RvE1, an anti-inflammatory and proResolvin lipid mediator derived from the omega-3 fatty acid EPA, decreased tumor growth in both the Wt and Tg mice and resulted in reduced cancer cell proliferation and angiogenesis. RvE1 treatment led to the destruction of the center of the solid tumor with viable tumor cells observed only at the periphery. The space between tumor cells was enlarged, with shrinking spindle-shaped nuclei inside. There was a marked increase in the extent of necrosis of the tumor core. The impact of RvE1 administration was more pronounced in Tg animals compared to Wt with a higher degree of necrosis and decreased vascularization. These observations suggest a profound chemopreventive impact of RvE1 treatment and support our hypothesis that increased availability of its receptor enhances its anti-cancer activity. Taken together with reduced pro-inflammatory cytokine expression and markers of angiogenesis, the data suggest that the mechanism of RvE1 action involves resolution of the inflammatory process in the micro-environment of the tumor tissue limiting angiogenesis and tumor growth and viability.

The tissue expression of pro-inflammatory markers was studied to quantify the actions of RvE1. The levels of G-CSF, IL-1α, IL-6, IL-8, IL-12 and TNFα were elevated in cancer tissues of both Wt and Tg mice. Infiltrating neoplastic and stromal cells cells can contribute to the tumor microenvironment through the secretion of growth factors, cytokines and chemokines (Arendt et al., 2010). These results are in concordance with other reports as well (Grasso et al., 2015, Helm et al., 2014). RvE1 treatment significantly reduces the levels of these cytokines in both Wt and Tg mice with more pronounced impact in Tg animals.

Another source of these local cytokines has been reported to be tumor-associated macrophages (TAMs), which dominate the immune infiltrate in tumors representing a key cell type linking inflammation and cancer (Barnes, 2014, Conway et al., 2016). TAMs in established tumors are generally skewed toward the M2-like phenotype, promoting tumor survival, progression, and dissemination through enhanced angiogenesis, epithelial-mesenchymal transition, and immune suppression (Bingle et al., 2002). While macrophage polarization has been suggested to play role in tumor progression and varies with the stage of different cancer forms, inflammatory changes in the microenvironment and their interaction with the genetic factors seem to be the driving force for oncogenesis (Conway et al., 2016).

Taken together with the previous observations that CD68+ macrophages were detected in both stroma and tumor cell islets with an inverse relationship between survival and stromal macrophage density (Welsh et al., 2005), the role of the macrophage can be bi-phasic, where macrophages can both be the part of the initiation and resolution of the inflammatory process. The data, while not focused on identification of macrophage phenotype and their role in cancer suggest that cytokine generation is suppressed by the actions of the RvE1; this impact was enhanced in Tg animals overexpressing the receptor for RvE1, and overall these "anti-inflammatory" activities were in parallel with tumor shrinkage and increased core necrosis.

To further study the mechanism of inflammation, the alterations in molecular regulators of inflammation (COX-2 and NF-κB) were investigated. Both were increased in cancerous tissues. COX-2 converts arachidonic acid in the cytoplasmic membrane into prostaglandin $E_2$ ($PGE_2$), which then regulates cell proliferation, differentiation, and apoptosis through several autocrine and paracrine pathways (Kudryavtsev et al., 2002). Inflammatory cytokines cause the activation of NF-κB, which in turn increases pro-inflammatory cytokine production and regulates expression of target genes with key roles in the inhibition of apoptosis and promotion of tumor growth (Khan et al., 2013). Hence, the increased expression of these genes in the current study suggested a strong role for the inflammatory process during the development of cancer. Pre-treatment with RvE1 resulted in a significant decrease in the expression of NF-κB and COX-2. This observation was in line with a recently published study where supplementation with DHA, which is an omega-3 fatty acid and precursor of D series Resolvins, inhibited COX-2 expression and induced apoptosis in WM266-4 metastatic melanoma cell line (Serini et al., 2012). Supplementation of fish oil also decreased COX-2 expression and inhibited the pathogenesis of colon cancer in rats (Kansal et al., 2014). Hence, regression of the expression of NF-κB and COX-2 in response to pre-treatment with RvE1, suggests chemopreventive actions by RvE1. Decrease in the expression of these genes was more marked in Tg animals suggesting that over-expression and therefore the bioavailability of ERV1 resulted in increased resolution of inflammation and cancer.

Cell proliferation was measured by the expression of Ki67 in tumor tissues. Ki-67 is present in all the dividing cells that define the increased cell proliferation in cancerous tissue. Abnormal epithelial proliferation is a hallmark of tumorigenesis and increased Ki-67 expression is observed in cancer (Mao et al., 2011, Birajdar et al., 2014). In this study, animals with cancer demonstrated an increased number of Ki-67 positive cells. In response to RvE1, the percentage of Ki-67 positive cells was decreased in both Wt and Tg animals. The decrease was more marked in Tg mice as compared to Wt mice, suggesting a direct impact of RvE1 on cancer cell proliferation. A recently published study links the reduction of cancer cell proliferation in lung cancer to the activities of TAMs, where their depletion resulted in reduced tumor growth (Fritz et al., 2014).

The histological data further document that RvE1 resulted in the necrosis of the central part of tumors. It was hypothesize that this phenomenon is associated with decreased vascularization/angiogenesis and analyzed the extent of micro-vessel density by immunohistochemical staining of CD31 and CD34. Strong CD31 and CD34 staining in the tumor tissues suggested an increase in neovascularization in parallel with previous reports (Bishayee et al., 2010, Wang et al., 2009). As angiogenesis is essential for the growth and maintenance of solid tumors, without vascularization, tumors cannot grow beyond a few millimeters in size and will become necrotic (Bishayee et al., 2010). In response to pre-treatment with RvE1, the extent of micro-vessel density was decreased in both the Wt and Tg animals. Ang-1 and Ang-2, ligands for the Tie-2 receptor expressed on endothelial cells, play a critical role in angiogenesis, in the presence of VEGF. A strong immunochemical staining and increased expression of VEGF, Ang-1 and Ang-2 was observed in the cancer tissue. This observation was well correlated with increased microvascular density data. Ang-1 and Ang-2 are functionally antagonistic molecules regulating angiogenesis. Ang-1 stabilizes blood vessels by promoting the interaction between endothelial cells and the surrounding extracellular matrix, and Ang-2 antagonizes the stabilizing action of Ang-1 by binding to Tie-2 competitively, which destabilizes vessels (Suri et al., 1996, Park et al., 2007). However, the vessels destabilized by Ang-2 do not regress, but undergo angiogenic changes in the presence of angiogenic factors such as VEGF (Holash et al., 1999, Lobov et al., 2002). Hence, the increased expression of both Ang-1 and Ang-2 in the presence of VEGF in our study suggests the involvement of multiple pathways of increased vascularization. Similar to blood vessels, pretreatment with RvE1 resulted in a significant attenuation of VEGF expression, Ang-1 and Ang-2, which further suggests that RvE1 abrogates the angiogenic response in cancer tissue by down-regulating VEGF. This decrease was more marked in Tg mice indicating that overexpression of ERV1 amplifies the activity of RvE1. These results also indicate that the attenuation of vascularization may represent a novel mechanism for the chemopreventive activity of RvE1 in cancer pathogenesis.

REFERENCES

1. Arendt, L. M., Rudnick, J. A., Keller, P. J. & Kuperwasser, C. (2010) Stroma in breast development and disease. *Semin Cell Dev Biol* 21, 11-18. doi:10.1016/j.semcdb.2009.10.003.
2. Arita, M., Bianchini, F., Aliberti, J., Sher, A., Chiang, N., Hong, S., Yang, R., Petasis, N. A. & Serhan, C. N. (2005a) Stereochemical assignment, antiinflammatory properties, and receptor for the omega-3 lipid mediator Resolvin E1. *J Exp Med* 201, 713-722. doi:10.1084/jem.20042031.
3. Arita, M., Oh, S. F., Chonan, T., Hong, S., Elangovan, S., Sun, Y. P., Uddin, J., Petasis, N. A. & Serhan, C. N. (2006) Metabolic inactivation of Resolvin E1 and stabilization of its anti-inflammatory actions. *J Biol Chem* 281, 22847-22854. doi:10.1074/jbc.M603766200.
4. Arita, M., Yoshida, M., Hong, S., Tjonahen, E., Glickman, J. N., Petasis, N. A., Blumberg, R. S. & Serhan, C. N. (2005b) Resolvin E1, an endogenous lipid mediator derived from omega-3 eicosapentaenoic acid, protects against 2,4,6-trinitrobenzene sulfonic acid-induced colitis. *Proc Natl Acad Sci USA* 102, 7671-7676. doi:10.1073/pnas.0409271102.
5. Barnes, P. J. (2014) Cellular and molecular mechanisms of chronic obstructive pulmonary disease. *Clin Chest Med* 35, 71-86. doi:10.1016/j.ccm.2013.10.004.
6. Bingle, L., Brown, N. J. & Lewis, C. E. (2002) The role of tumour-associated macrophages in tumour progression: implications for new anticancer therapies. *J Pathol* 196, 254-265. doi:10.1002/path.1027.
7. Birajdar, S. S., Radhika, M., Paremala, K., Sudhakara, M., Soumya, M. & Gadivan, M. (2014) Expression of Ki-67 in normal oral epithelium, leukoplakic oral epithelium and oral squamous cell carcinoma. *J Oral Maxillofac Pathol* 18, 169-176. doi:10.4103/0973-029X.140729.
8. Bishayee, A., Waghray, A., Barnes, K. F., Mbimba, T., Bhatia, D., Chatterjee, M. & Darvesh, A. S. (2010) Suppression of the inflammatory cascade is implicated in resveratrol chemoprevention of experimental hepatocarcinogenesis. *Pharm Res* 27, 1080-1091. doi: 10.1007/s11095-010-0144-4.
9. Buckley, C. D., Pilling, D., Lord, J. M., Akbar, A. N., Scheel-Toellner, D. & Salmon, M. (2001) Fibroblasts regulate the switch from acute Resolving to chronic persistent inflammation. *Trends Immunol* 22, 199-204.
10. Campbell, E. L., Louis, N. A., Tomassetti, S. E., Canny, G. O., Arita, M., Serhan, C. N. & Colgan, S. P. (2007) Resolvin E1 promotes mucosal surface clearance of neutrophils: a new paradigm for inflammatory resolution. *FASEB J* 21, 3162-3170. doi:10.1096/fj.07-8473com.
11. Cash, J. L., Hart, R., Russ, A., Dixon, J. P., Colledge, W. H., Doran, J., Hendrick, A. G., Carlton, M. B. & Greaves, D. R. (2008) Synthetic chemerin-derived peptides suppress inflammation through ChemR23. *J Exp Med* 205, 767-775. doi:10.1084/jem.20071601.
12. Cho, W. C., Kwan, C. K., Yau, S., So, P. P., Poon, P. C. & Au, J. S. (2011) The role of inflammation in the pathogenesis of lung cancer. *Expert Opin Ther Targets* 15, 1127-1137. doi:10.1517/14728222.2011.599801.
13. Colotta, F., Allavena, P., Sica, A., Garlanda, C. & Mantovani, A. (2009) Cancer-related inflammation, the seventh hallmark of cancer: links to genetic instability. *Carcinogenesis* 30, 1073-1081. doi:10.1093/carcin/bgp127.
14. Connor, K. M., SanGiovanni, J. P., Lofqvist, C., Aderman, C. M., Chen, J., Higuchi, A., Hong, S., Pravda, E. A., Majchrzak, S., Carper, D., Hellstrom, A., Kang, J. X., Chew, E. Y., Salem, N., Jr., Serhan, C. N. & Smith, L. E. (2007) Increased dietary intake of omega-3-polyunsaturated fatty acids reduces pathological retinal angiogenesis. *Nat Med* 13, 868-873. doi:10.1038/nm1591.
15. Conway, E. M., Pikor, L. A., Kung, S. H., Hamilton, M. J., Lam, S., Lam, W. L. & Bennewith, K. L. (2016) Macrophages, Inflammation, and Lung Cancer. *Am J Respir Crit Care Med* 193, 116-130. doi:10.1164/rccm.201508-1545CI.
16. Coussens, L. M. & Werb, Z. (2002) Inflammation and cancer. *Nature* 420, 860-867. doi:10.1038/nature01322.
17. Ferreccio, C., Yuan, Y., Calle, J., Benitez, H., Parra, R. L., Acevedo, J., Smith, A. H., Liaw, J. & Steinmaus, C. (2013) Arsenic, tobacco smoke, and occupation: associations of multiple agents with lung and bladder cancer. *Epidemiology* 24, 898-905. doi:10.1097/EDE.0b013e31829e3e03.
18. Fitzpatrick, F. A. (2001) Inflammation, carcinogenesis and cancer. *Int Immunopharmacol* 1, 1651-1667.
19. Fritz, J. M., Tennis, M. A., Orlicky, D. J., Lin, H., Ju, C., Redente, E. F., Choo, K. S., Staab, T. A., Bouchard, R. J., Merrick, D. T., Malkinson, A. M. & Dwyer-Nield, L. D. (2014) Depletion of tumor-associated macrophages slows the growth of chemically induced mouse lung adenocarcinomas. *Front Immunol* 5, 587. doi: 10.3389/fimmu.2014.00587.
20. Gao, L., Faibish, D., Fredman, G., Herrera, B. S., Chiang, N., Serhan, C. N., Van Dyke, T. E. & Gyurko, R. (2013) Resolvin E1 and chemokine-like receptor 1 mediate bone preservation. *J Immunol* 190, 689-694. doi: 10.4049/jimmunol.1103688.
21. Gomes, M., Teixeira, A. L., Coelho, A., Araujo, A. & Medeiros, R. (2014) The role of inflammation in lung cancer. *Adv Exp Med Biol* 816, 1-23. doi:10.1007/978-3-0348-0837-8_1.
22. Grasso, F., Di Meo, S., De Luca, G., Pasquini, L., Rossi, S., Boirivant, M., Biffoni, M., Bignami, M. & Di Carlo, E. (2015) The MUTYH base excision repair gene protects against inflammation-associated colorectal carcinogenesis. *Oncotarget* 6, 19671-19684.
23. Hanahan, D. & Weinberg, R. A. (2011) Hallmarks of cancer: the next generation. *Cell* 144, 646-674. doi: 10.1016/j.cell.2011.02.013.

24. Hasturk, H., Kantarci, A., Ohira, T., Arita, M., Ebrahimi, N., Chiang, N., Petasis, N. A., Levy, B. D., Serhan, C. N. & Van Dyke, T. E. (2006) RvE1 protects from local inflammation and osteoclast-mediated bone destruction in periodontitis. *FASEB J* 20, 401-403. doi:10.1096/fj.05-4724fje.

25. Heinrich, E. L., Walser, T. C., Krysan, K., Liclican, E. L., Grant, J. L., Rodriguez, N. L. & Dubinett, S. M. (2012) The inflammatory tumor microenvironment, epithelial mesenchymal transition and lung carcinogenesis. *Cancer Microenviron* 5, 5-18. doi:10.1007/s12307-011-0089-0.

26. Helm, O., Held-Feindt, J., Grage-Griebenow, E., Reiling, N., Ungefroren, H., Vogel, I., Kruger, U., Becker, T., Ebsen, M., Rocken, C., Kabelitz, D., Schafer, H. & Sebens, S. (2014) Tumor-associated macrophages exhibit pro- and anti-inflammatory properties by which they impact on pancreatic tumorigenesis. *Int J Cancer* 135, 843-861. doi:10.1002/ijc.28736.

27. Herrera, B. S., Hasturk, H., Kantarci, A., Freire, M. O., Nguyen, O., Kansal, S. & Van Dyke, T. E. (2015) Impact of Resolvin E1 on murine neutrophil phagocytosis in type 2 diabetes. *Infect Immun* 83, 792-801. doi:10.1128/IAI.02444-14.

28. Holash, J., Wiegand, S. J. & Yancopoulos, G. D. (1999) New model of tumor angiogenesis: dynamic balance between vessel regression and growth mediated by angiopoietins and VEGF. *Oncogene* 18, 5356-5362. doi:10.1038/sj.onc.1203035.

29. Houghton, A. M., Mouded, M. & Shapiro, S. D. (2008) Common origins of lung cancer and COPD. *Nat Med* 14, 1023-1024. doi:10.1038/nm1008-1023.

30. Kansal, S., Bhatnagar, A. & Agnihotri, N. (2014) Fish oil suppresses cell growth and metastatic potential by regulating PTEN and NF-kappaB signaling in colorectal cancer. *PLoS One* 9, e84627. doi:10.1371/journal.pone.0084627.

31. Khan, S., Lopez-Dee, Z., Kumar, R. & Ling, J. (2013) Activation of NFkB is a novel mechanism of pro-survival activity of glucocorticoids in breast cancer cells. *Cancer Lett* 337, 90-95. doi:10.1016/j.canlet.2013.05.020.

32. Kudryavtsev, I. A., Golenko, O. D., Gudkova, M. V. & Myasishcheva, N. V. (2002) Arachidonic acid metabolism in growth control of A549 human lung adenocarcinoma cells. *Biochemistry (Mosc)* 67, 1021-1026.

33. Lee, H. J., Park, J. M., Han, Y. M., Gil, H. K., Kim, J., Chang, J. Y., Jeong, M., Go, E. J. & Hahm, K. B. (2015) The role of chronic inflammation in the development of gastrointestinal cancers: reviewing cancer prevention with natural anti-inflammatory intervention. *Expert Rev Gastroenterol Hepatol*, 1-11. doi:10.1586/17474124.2016.1103179.

34. Lee, H. J., Park, M. K., Lee, E. J. & Lee, C. H. (2013) Resolvin D1 inhibits TGF-beta1-induced epithelial mesenchymal transition of A549 lung cancer cells via lipoxin A4 receptor/formyl peptide receptor 2 and GPR32. *Int J Biochem Cell Biol* 45, 2801-2807. doi:10.1016/j.biocel.2013.09.018.

35. Lobov, I. B., Brooks, P. C. & Lang, R. A. (2002) Angiopoietin-2 displays VEGF-dependent modulation of capillary structure and endothelial cell survival in vivo. *Proc Natl Acad Sci USA* 99, 11205-11210. doi:10.1073/pnas.172161899.

36. Lu, H., Ouyang, W. & Huang, C. (2006) Inflammation, a key event in cancer development. *Mol Cancer Res* 4, 221-233. doi:10.1158/1541-7786.MCR-05-0261.

37. Maderna, P. & Godson, C. (2003) Phagocytosis of apoptotic cells and the resolution of inflammation. *Biochim Biophys Acta* 1639, 141-151.

38. Maeda, S. & Omata, M. (2008) Inflammation and cancer: role of nuclear factor-kappaB activation. *Cancer Sci* 99, 836-842. doi:10.1111/j.1349-7006.2008.00763.x.

39. Mao, J. T., Roth, M. D., Fishbein, M. C., Aberle, D. R., Zhang, Z. F., Rao, J. Y., Tashkin, D. P., Goodglick, L., Holmes, E. C., Cameron, R. B., Dubinett, S. M., Elashoff, R., Szabo, E. & Elashoff, D. (2011) Lung cancer chemoprevention with celecoxib in former smokers. *Cancer Prev Res (Phila)* 4, 984-993. doi:10.1158/1940-6207.CAPR-11-0078.

40. Park, J. H., Park, K. J., Kim, Y. S., Sheen, S. S., Lee, K. S., Lee, H. N., Oh, Y. J. & Hwang, S. C. (2007) Serum angiopoietin-2 as a clinical marker for lung cancer. *Chest* 132, 200-206. doi:10.1378/chest.06-2915.

41. Parolini, S., Santoro, A., Marcenaro, E., Luini, W., Massardi, L., Facchetti, F., Communi, D., Parmentier, M., Majorana, A., Sironi, M., Tabellini, G., Moretta, A. & Sozzani, S. (2007) The role of chemerin in the colocalization of NK and dendritic cell subsets into inflamed tissues. *Blood* 109, 3625-3632. doi:10.1182/blood-2006-08-038844.

42. Poczobutt, J. M., Gijon, M., Amin, J., Hanson, D., Li, H., Walker, D., Weiser-Evans, M., Lu, X., Murphy, R. C. & Nemenoff, R. A. (2013) Eicosanoid profiling in an orthotopic model of lung cancer progression by mass spectrometry demonstrates selective production of leukotrienes by inflammatory cells of the microenvironment. *PLoS One* 8, e79633. doi:10.1371/journal.pone.0079633.

43. Serhan, C. N., Arita, M., Hong, S. & Gotlinger, K. (2004) Resolvins, docosatrienes, and neuroprotectins, novel omega-3-derived mediators, and their endogenous aspirin-triggered epimers. *Lipids* 39, 1125-1132.

44. Serhan, C. N., Clish, C. B., Brannon, J., Colgan, S. P., Chiang, N. & Gronert, K. (2000) Novel functional sets of lipid-derived mediators with antiinflammatory actions generated from omega-3 fatty acids via cyclooxygenase 2-nonsteroidal antiinflammatory drugs and transcellular processing. *J Exp Med* 192, 1197-1204.

45. Serhan, C. N., Hong, S., Gronert, K., Colgan, S. P., Devchand, P. R., Mirick, G. & Moussignac, R. L. (2002) Resolvins: a family of bioactive products of omega-3 fatty acid transformation circuits initiated by aspirin treatment that counter proinflammation signals. *J Exp Med* 196, 1025-1037.

46. Serini, S., Fasano, E., Piccioni, E., Monego, G., Cittadini, A. R., Celleno, L., Ranelletti, F. O. & Calviello, G. (2012) DHA induces apoptosis and differentiation in human melanoma cells in vitro: involvement of HuR-mediated COX-2 mRNA stabilization and beta-catenin nuclear translocation. *Carcinogenesis* 33, 164-173. doi:10.1093/carcin/bgr240.

47. Shi, L., Wang, L., Hou, J., Zhu, B., Min, Z., Zhang, M., Song, D., Cheng, Y. & Wang, X. (2015) Targeting roles of inflammatory microenvironment in lung cancer and metastasis. *Cancer Metastasis Rev* 34, 319-331. doi:10.1007/s10555-015-9570-4.

48. Suri, C., Jones, P. F., Patan, S., Bartunkova, S., Maisonpierre, P. C., Davis, S., Sato, T. N. & Yancopoulos, G. D. (1996) Requisite role of angiopoietin-1, a ligand for the TIE2 receptor, during embryonic angiogenesis. *Cell* 87, 1171-1180.

49. Wang, W., Xu, G. L., Jia, W. D., Wang, Z. H., Li, J. S., Ma, J. L., Ge, Y. S., Xie, S. X. & Yu, J. H. (2009) Expression and correlation of hypoxia-inducible factor-lalpha, vascular endothelial growth factor and microvessel density in experimental rat hepatocarcinogenesis. *J Int Med Res* 37, 417-425.

50. Welsh, T. J., Green, R. H., Richardson, D., Waller, D. A., O'Byrne, K. J. & Bradding, P. (2005) Macrophage and mast-cell invasion of tumor cell islets confers a marked survival advantage in non-small-cell lung cancer. *J Clin Oncol* 23, 8959-8967. doi:10.1200/JCO.2005.01.4910.

51. Wittamer, V., Franssen, J. D., Volcano, M., Mirjolet, J. F., Le Poul, E., Migeotte, I., Brezillon, S., Tyldesley, R., Blanpain, C., Detheux, M., Mantovani, A., Sozzani, S., Vassart, G., Parmentier, M. & Communi, D. (2003) Specific recruitment of antigen-presenting cells by chemerin, a novel processed ligand from human inflammatory fluids. *J Exp Med* 198, 977-985. doi: 10.1084/jem.20030382.

INCORPORATION BY REFERENCE

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

EQUIVALENTS

Although the foregoing subject matter has been described in some detail by way of illustration and example for purposes of clarity of understanding, it will be understood by those skilled in the art that certain changes and modifications can be practiced within the scope of the appended claims.

What is claimed:

1. A method for treating lung cancer in a subject, wherein the subject comprises cells that overexpress Receptor for Resolvin E1 (ERV1), the method comprising:
    administering at least one Resolvin E series lipid agonist to the subject, wherein the at least one Resolvin E series lipid agonist is selected from the group consisting of di-hydroxy members of the Resolvin E series and tri-hydroxy members of the Resolvin E series.

2. The method of claim 1, wherein the at least one Resolvin E series lipid agonist is selected from the group consisting of Resolvin E1, Resolvin E2, and Resolvin E3.

3. The method of claim 1, wherein the at least one Resolvin E series lipid agonist comprises Resolvin E 1.

4. The method of claim 1, wherein the at least one Resolvin E series lipid agonist is administered systemically, wherein the systemic administration is selected from the group consisting of oral, intravenous, intradermal, intraperitoneal, subcutaneous, and intramuscular administration.

5. The method of claim 1, wherein the at least one Resolvin E series lipid agonist is administered intratumorally or peritumorally.

6. The method of claim 1, wherein the subject is treated with at least one additional anti-cancer agent, wherein the anti-cancer agent is selected from the group consisting of paclitaxel, cisplatin, topotecan, gemcitabine, bleomycin, etoposide, carboplatin, docetaxel, doxorubicin, topotecan, cyclophosphamide, trabectedin, olaparib, tamoxifen, letrozole, and bevacizumab.

7. The method of claim 1, wherein the subject is concurrently treated with cisplatin.

8. The method of claim 1, wherein the subject is treated with at least one additional anti-cancer therapy, wherein the anti-cancer therapy is radiation therapy, chemotherapy, or surgery.

9. The method of claim 1, wherein the subject is a mammal.

10. The method of claim 1, wherein the subject is a human.

11. The method of claim 1, wherein an inflammatory response is inhibited or reduced in the subject, wherein the inhibition or reduction in the inflammatory response results in a decreased expression of the NF-κB, IL-6, and IL-8 genes.

12. The method of claim 1, wherein an angiogenic response is inhibited or reduced in the subject, wherein the inhibition or reduction in the angiogenic response results in a decreased expression of the Ang1, Ang2, and VEGF genes.

13. The method of claim 1, wherein malignancy is inhibited or reduced in the subject.

14. The method of claim 1, wherein tumor necrosis is enhanced or increased in the subject.

* * * * *